US009339332B2

(12) United States Patent
Srivastava

(10) Patent No.: US 9,339,332 B2
(45) Date of Patent: May 17, 2016

(54) NEUROMODULATION CATHETERS WITH NERVE MONITORING FEATURES FOR TRANSMITTING DIGITAL NEURAL SIGNALS AND ASSOCIATED SYSTEMS AND METHODS

(71) Applicant: Medtronic Ardian Luxembourg S.a.r.l., Luxembourg (LU)

(72) Inventor: Nishant R. Srivastava, Mountain View, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 214 days.

(21) Appl. No.: 14/015,835

(22) Filed: Aug. 30, 2013

(65) Prior Publication Data

US 2015/0066007 A1   Mar. 5, 2015

(51) Int. Cl.
*A61B 18/14* (2006.01)
*A61B 17/32* (2006.01)
(Continued)

(52) U.S. Cl.
CPC ......... *A61B 18/1492* (2013.01); *A61B 5/04001* (2013.01); *A61B 5/6852* (2013.01); *A61B 17/320068* (2013.01); *A61B 18/02* (2013.01); *A61B 2017/00039* (2013.01); *A61B 2018/0022* (2013.01); *A61B 2018/00267* (2013.01); *A61B 2018/00404* (2013.01);
(Continued)

(58) Field of Classification Search
CPC ........... A61B 2018/00267; A61B 2018/00279; A61B 2018/00434; A61B 2018/00988; A61B 2018/1435; A61B 2018/00511; A61B 5/6857; A61B 2017/00039

USPC ................. 606/41, 34; 607/99, 113, 127, 131
See application file for complete search history.

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| EP | 1169976 | 1/2002 |
| EP | 2316371 | 5/2011 |

(Continued)

OTHER PUBLICATIONS

European Search Report for European Application No. 13159256, Date Mailed: Oct. 17, 2013, 6 pages.

(Continued)

*Primary Examiner* — Joseph Stoklosa
*Assistant Examiner* — Thomas Giuliani

(57) ABSTRACT

Neuromodulation catheters with nerve monitoring features for transmitting digital neural signals and associated systems and methods are disclosed herein. A neuromodulation catheter configured in accordance with some embodiments of the present technology can include, for example, a handle and an elongated shaft attached to the handle. The shaft can have a proximal portion and a distal portion configured to be moved within a lumen of a blood vessel of a human patient. The neuromodulation catheter can further include an array of contacts at the distal portion of the shaft and a digitizer at the handle or the shaft. The contacts can be configured to detect analog neural signals from within the blood vessel. The digitizer can be configured to receive the analog neural signals from the contacts, digitize the analog neural signals into digital neural signals, and transmit the digital neural signals to a read/write module external to the patient.

21 Claims, 14 Drawing Sheets

(51) Int. Cl.
  *A61B 18/02*  (2006.01)
  *A61B 5/04*  (2006.01)
  *A61B 5/00*  (2006.01)
  A61B 17/00  (2006.01)
  A61B 18/00  (2006.01)
  A61N 7/02  (2006.01)

(52) U.S. Cl.
  CPC ........... *A61B 2018/00434* (2013.01); *A61B 2018/00511* (2013.01); *A61B 2018/00577* (2013.01); *A61B 2018/00642* (2013.01); *A61B 2018/0212* (2013.01); *A61B 2018/1435* (2013.01); *A61B 2018/1467* (2013.01); *A61N 7/022* (2013.01)

(56) References Cited

U.S. PATENT DOCUMENTS

| | | | |
|---|---|---|---|
| 4,709,698 A | 12/1987 | Johnston et al. | |
| 4,750,499 A * | 6/1988 | Hoffer | 607/116 |
| 4,764,504 A | 8/1988 | Johnson et al. | |
| 4,890,623 A | 1/1990 | Cook et al. | |
| 4,976,711 A | 12/1990 | Parins et al. | |
| 5,300,068 A | 4/1994 | Rosar et al. | |
| 5,358,514 A | 10/1994 | Schulman et al. | |
| 5,368,591 A | 11/1994 | Lennox et al. | |
| 5,423,744 A | 6/1995 | Gencheff et al. | |
| 5,425,364 A | 6/1995 | Imran | |
| 5,484,400 A | 1/1996 | Edwards et al. | |
| 5,571,147 A | 11/1996 | Sluijter et al. | |
| 5,588,964 A | 12/1996 | Imran et al. | |
| 5,599,345 A | 2/1997 | Edwards et al. | |
| 5,626,576 A | 5/1997 | Janssen | |
| 5,672,174 A | 9/1997 | Gough et al. | |
| 5,688,266 A | 11/1997 | Edwards et al. | |
| 5,700,282 A | 12/1997 | Zabara | |
| 5,707,400 A | 1/1998 | Terry, Jr. et al. | |
| 5,772,590 A | 6/1998 | Webster, Jr. | |
| 5,860,974 A | 1/1999 | Abele | |
| 5,865,787 A | 2/1999 | Shapland et al. | |
| 5,893,885 A | 4/1999 | Webster et al. | |
| 5,944,710 A | 8/1999 | Dev et al. | |
| 5,954,719 A | 9/1999 | Chen et al. | |
| 5,983,141 A | 11/1999 | Sluijter et al. | |
| 6,004,269 A | 12/1999 | Crowley et al. | |
| 6,009,877 A | 1/2000 | Edwards | |
| 6,024,740 A | 2/2000 | Lesh et al. | |
| 6,036,687 A | 3/2000 | Laufer et al. | |
| 6,066,134 A | 5/2000 | Eggers et al. | |
| 6,091,995 A | 7/2000 | Ingle et al. | |
| 6,099,524 A | 8/2000 | Lipson et al. | |
| 6,117,101 A | 9/2000 | Diederich et al. | |
| 6,135,999 A | 10/2000 | Fanton et al. | |
| 6,149,620 A | 11/2000 | Baker et al. | |
| 6,161,048 A | 12/2000 | Sluijter et al. | |
| 6,219,577 B1 | 4/2001 | Brown, III et al. | |
| 6,224,592 B1 | 5/2001 | Eggers et al. | |
| 6,246,912 B1 | 6/2001 | Sluijter et al. | |
| 6,273,886 B1 | 8/2001 | Edwards et al. | |
| 6,283,951 B1 | 9/2001 | Flaherty et al. | |
| 6,292,695 B1 | 9/2001 | Webster, Jr. et al. | |
| 6,314,325 B1 | 11/2001 | Fitz | |
| 6,322,558 B1 | 11/2001 | Taylor et al. | |
| 6,322,559 B1 | 11/2001 | Daulton et al. | |
| 6,405,732 B1 | 6/2002 | Edwards et al. | |
| 6,413,255 B1 | 7/2002 | Stern | |
| 6,488,679 B1 | 12/2002 | Swanson et al. | |
| 6,506,189 B1 | 1/2003 | Rittman, III et al. | |
| 6,514,226 B1 | 2/2003 | Levin et al. | |
| 6,522,926 B1 | 2/2003 | Kieval et al. | |
| 6,542,781 B1 | 4/2003 | Koblish et al. | |
| 6,562,034 B2 | 5/2003 | Edwards et al. | |
| 6,616,624 B1 | 9/2003 | Kieval | |
| 6,622,731 B2 | 9/2003 | Daniel et al. | |
| 6,635,054 B2 | 10/2003 | Fjield et al. | |
| 6,685,648 B2 | 2/2004 | Flaherty et al. | |
| 6,711,444 B2 | 3/2004 | Koblish | |
| 6,736,835 B2 | 5/2004 | Pellegrino et al. | |
| 6,752,805 B2 | 6/2004 | Maguire et al. | |
| 6,845,267 B2 | 1/2005 | Harrison et al. | |
| 6,850,801 B2 | 2/2005 | Kieval et al. | |
| 6,869,431 B2 | 3/2005 | Maguire et al. | |
| 6,885,888 B2 | 4/2005 | Rezai | |
| 6,893,436 B2 | 5/2005 | Woodard et al. | |
| 6,939,346 B2 | 9/2005 | Kannenberg et al. | |
| 7,149,574 B2 | 12/2006 | Yun et al. | |
| 7,160,296 B2 | 1/2007 | Pearson et al. | |
| 7,162,303 B2 | 1/2007 | Levin et al. | |
| 7,221,979 B2 | 5/2007 | Zhou et al. | |
| 7,381,200 B2 | 6/2008 | Katoh et al. | |
| 7,390,894 B2 | 6/2008 | Weinshilboum et al. | |
| 7,617,005 B2 | 11/2009 | Demarais et al. | |
| 7,620,451 B2 | 11/2009 | Demarais et al. | |
| 7,647,115 B2 | 1/2010 | Levin et al. | |
| 7,653,438 B2 | 1/2010 | Deem et al. | |
| 7,717,948 B2 | 5/2010 | Demarais et al. | |
| 7,778,703 B2 | 8/2010 | Gross et al. | |
| 8,131,371 B2 | 3/2012 | Demarais et al. | |
| 8,131,372 B2 | 3/2012 | Levin et al. | |
| 8,140,170 B2 | 3/2012 | Rezai et al. | |
| 8,145,317 B2 | 3/2012 | Demarais et al. | |
| 8,150,518 B2 | 4/2012 | Levin et al. | |
| 8,150,519 B2 | 4/2012 | Demarais et al. | |
| 8,150,520 B2 | 4/2012 | Demarais et al. | |
| 8,175,711 B2 | 5/2012 | Demarais et al. | |
| 8,447,392 B2 * | 5/2013 | Llinas | 600/544 |
| 8,702,619 B2 | 4/2014 | Wang | |
| 8,768,470 B2 | 7/2014 | Deem et al. | |
| 8,909,316 B2 | 12/2014 | Ng | |
| 8,977,359 B2 | 3/2015 | Rossing | |
| 9,002,446 B2 | 4/2015 | Wenzel et al. | |
| 9,014,809 B2 | 4/2015 | Wenzel et al. | |
| 9,014,821 B2 | 4/2015 | Wang | |
| 2002/0087208 A1 | 7/2002 | Koblish et al. | |
| 2002/0107515 A1 | 8/2002 | Edwards et al. | |
| 2002/0139379 A1 | 10/2002 | Edwards et al. | |
| 2002/0165532 A1 * | 11/2002 | Hill et al. | 606/41 |
| 2002/0183682 A1 | 12/2002 | Darvish et al. | |
| 2003/0050635 A1 | 3/2003 | Truckai et al. | |
| 2003/0050681 A1 | 3/2003 | Pianca et al. | |
| 2003/0060858 A1 | 3/2003 | Kieval et al. | |
| 2003/0074039 A1 | 4/2003 | Puskas | |
| 2003/0125790 A1 | 7/2003 | Fastovsky et al. | |
| 2003/0181897 A1 | 9/2003 | Thomas et al. | |
| 2003/0199863 A1 | 10/2003 | Swanson et al. | |
| 2003/0216792 A1 | 11/2003 | Levin et al. | |
| 2003/0233099 A1 | 12/2003 | Danaek et al. | |
| 2004/0010289 A1 | 1/2004 | Biggs et al. | |
| 2004/0215186 A1 | 10/2004 | Cornelius et al. | |
| 2005/0080409 A1 | 4/2005 | Young et al. | |
| 2005/0187579 A1 | 8/2005 | Danek et al. | |
| 2005/0228460 A1 | 10/2005 | Levin et al. | |
| 2006/0085054 A1 | 4/2006 | Zikorus et al. | |
| 2006/0095029 A1 | 5/2006 | Young et al. | |
| 2006/0100618 A1 | 5/2006 | Chan et al. | |
| 2006/0206150 A1 | 9/2006 | Demarais et al. | |
| 2006/0212076 A1 | 9/2006 | Demarais et al. | |
| 2006/0271111 A1 | 11/2006 | Demarais et al. | |
| 2006/0282127 A1 * | 12/2006 | Zealear | 607/42 |
| 2007/0129720 A1 | 6/2007 | Demarais et al. | |
| 2007/0265687 A1 | 11/2007 | Deem et al. | |
| 2008/0319513 A1 | 12/2008 | Pu et al. | |
| 2009/0036948 A1 | 2/2009 | Levin et al. | |
| 2010/0137860 A1 | 6/2010 | Demarais et al. | |
| 2010/0137952 A1 | 6/2010 | Demarais et al. | |
| 2010/0191112 A1 | 7/2010 | Demarais et al. | |
| 2010/0222851 A1 | 9/2010 | Deem et al. | |
| 2010/0222854 A1 | 9/2010 | Demarais et al. | |
| 2011/0112400 A1 | 5/2011 | Emery et al. | |
| 2011/0270120 A1 | 11/2011 | McFarlin et al. | |
| 2011/0306851 A1 | 12/2011 | Wang | |
| 2011/0307034 A1 | 12/2011 | Hastings et al. | |
| 2012/0029504 A1 | 2/2012 | Afonso et al. | |
| 2012/0123289 A1 * | 5/2012 | Sorenson et al. | 600/544 |

(56) References Cited

U.S. PATENT DOCUMENTS

| | | | |
|---|---|---|---|
| 2012/0123400 | A1 | 5/2012 | Francischelli et al. |
| 2012/0130289 | A1 | 5/2012 | Demarais et al. |
| 2012/0130345 | A1 | 5/2012 | Levin et al. |
| 2012/0143097 | A1 | 6/2012 | Pike, Jr. |
| 2012/0172837 | A1 | 7/2012 | Demarais et al. |
| 2012/0172870 | A1 | 7/2012 | Jenson et al. |
| 2012/0191079 | A1 | 7/2012 | Moll et al. |
| 2012/0265198 | A1 | 10/2012 | Crow et al. |
| 2012/0296232 | A1 | 11/2012 | Ng |
| 2012/0296329 | A1 | 11/2012 | Ng |
| 2013/0085489 | A1 | 4/2013 | Fain et al. |
| 2013/0123778 | A1 | 5/2013 | Richardson et al. |
| 2013/0131743 | A1 | 5/2013 | Yamasaki et al. |
| 2013/0165764 | A1 | 6/2013 | Scheuermann et al. |
| 2013/0172878 | A1 | 7/2013 | Smith |
| 2013/0218029 | A1 | 8/2013 | Cholette et al. |
| 2013/0274614 | A1 | 10/2013 | Shimada et al. |
| 2013/0282001 | A1 | 10/2013 | Hezi-Yamit et al. |
| 2014/0012133 | A1 | 1/2014 | Sverdlik et al. |
| 2014/0066803 | A1 | 3/2014 | Choi |
| 2014/0073903 | A1 | 3/2014 | Weber et al. |
| 2014/0074089 | A1 | 3/2014 | Nishii |
| 2014/0128865 | A1 | 5/2014 | Gross |
| 2014/0194866 | A1 | 7/2014 | Wang |
| 2014/0213873 | A1 | 7/2014 | Wang |
| 2014/0221805 | A1 | 8/2014 | Wang |
| 2014/0236137 | A1 | 8/2014 | Tran et al. |
| 2014/0236138 | A1 | 8/2014 | Tran et al. |
| 2014/0246465 | A1 | 9/2014 | Peterson et al. |
| 2014/0249524 | A1 | 9/2014 | Kocur |
| 2014/0266235 | A1 | 9/2014 | Mathur |
| 2014/0275924 | A1 | 9/2014 | Min et al. |
| 2014/0276124 | A1 | 9/2014 | Cholette et al. |
| 2014/0276733 | A1 | 9/2014 | VanScoy et al. |
| 2014/0276742 | A1 | 9/2014 | Nabutovsky et al. |
| 2014/0276746 | A1 | 9/2014 | Nabutovsky et al. |
| 2014/0276755 | A1 | 9/2014 | Cao et al. |
| 2014/0276762 | A1 | 9/2014 | Parsonage |
| 2014/0276766 | A1 | 9/2014 | Brotz et al. |
| 2014/0276767 | A1 | 9/2014 | Brotz et al. |
| 2014/0276773 | A1 | 9/2014 | Brotz et al. |
| 2014/0316400 | A1 | 10/2014 | Blix et al. |
| 2014/0316496 | A1 | 10/2014 | Masson et al. |
| 2014/0330267 | A1 | 11/2014 | Harrington |
| 2014/0336637 | A1 | 11/2014 | Agrawal et al. |
| 2015/0005764 | A1 | 1/2015 | Hanson et al. |
| 2015/0025524 | A1 | 1/2015 | Nabutovsky |
| 2015/0112329 | A1 | 4/2015 | Ng |

FOREIGN PATENT DOCUMENTS

| | | |
|---|---|---|
| EP | 2441408 | 4/2012 |
| EP | 2594193 | 5/2013 |
| EP | 2613704 | 7/2013 |
| EP | 2747691 | 7/2014 |
| EP | 2797535 | 11/2014 |
| WO | WO-2014091328 | 7/1989 |
| WO | WO-9407446 | 4/1994 |
| WO | WO-9525472 | 9/1995 |
| WO | WO-9531142 | 11/1995 |
| WO | WO-9736548 | 10/1997 |
| WO | WO-99/00060 | 1/1999 |
| WO | WO-0122897 | 4/2001 |
| WO | WO-0170114 | 9/2001 |
| WO | WO-03022167 | 3/2003 |
| WO | WO-03082080 | 10/2003 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO-2006105121 | 10/2006 |
| WO | WO-2007008954 | 1/2007 |
| WO | WO-2007078997 | 7/2007 |
| WO | WO-2008049084 | 4/2008 |
| WO | WO-2010078175 | 7/2010 |
| WO | WO-2012033974 | 3/2012 |
| WO | WO-2012158864 | 11/2012 |
| WO | WO-2013030738 | 3/2013 |
| WO | WO-2013030743 | 3/2013 |
| WO | WO-2013074813 | 5/2013 |
| WO | WO-2013101485 | 7/2013 |
| WO | WO-2013112844 | 8/2013 |
| WO | WO-2014012282 | 1/2014 |
| WO | WO-2014029355 | 2/2014 |
| WO | WO-2014059165 | 4/2014 |
| WO | WO-2014068577 | 5/2014 |
| WO | WO-2014070999 | 5/2014 |
| WO | WO-2014091401 | 6/2014 |
| WO | WO-2014/149550 | 9/2014 |
| WO | WO-2014/149552 | 9/2014 |
| WO | WO-2014/149553 | 9/2014 |
| WO | WO-2014/149690 | 9/2014 |
| WO | WO-2014150425 | 9/2014 |
| WO | WO-2014150432 | 9/2014 |
| WO | WO-2014150441 | 9/2014 |
| WO | WO-2014150455 | 9/2014 |
| WO | WO-2014/158713 | 10/2014 |
| WO | WO-2014158708 | 10/2014 |
| WO | WO-2014163990 | 10/2014 |
| WO | WO-2014/179768 | 11/2014 |
| WO | WO-2014/182946 | 11/2014 |

OTHER PUBLICATIONS

U.S. Appl. No. 95/002,110, filed Aug. 29, 2012, Demarais et al.
U.S. Appl. No. 95/002,209, filed Sep. 13, 2012, Levin et al.
U.S. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.

(56) References Cited

OTHER PUBLICATIONS

"Neurotech Reports Announces Winners of Gold Electrode Awards." Neurotech business report, 2009. 1 page. <http://www.neurotechreports.com/pages/goldelectrodes09.html>.

"Quick. Consistent. Controlled. OneShot renal Denervation System" [Brochure], Covidien: positive results for life, 2013, (n.l.), 4 pages.

"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.

"The Edison Awards™" Edison Awards: Honoring Innovations & Innovators, 2013, 2 pages, <http://www.edisonawards.com/Awards.php>.

"The Future of Renal denervation for the Treatment of Resistant Hypertension." St. Jude Medical, Inc., 2012, 12 pages.

"Vessix Renal Denervation System: So Advanced Its Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul Integr Comp Physiol, vol. 274, 1998, 7 pages.

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.

Benito, F., et al. "Radiofrequency catheter ablation of accessory pathways in infants." Heart, 78:160-162 (1997).

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global SYMPLICITY registry." EuroIntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Dibona, G.F. "Sympathetic nervous system and kidney in hypertension." Nephrol and Hypertension, 11: 197-200 (2002).

Dubuc, M., et al., "Feasibility of cardiac cryoablation using a transvenous steerable electrode catheter." J Interv Cardiac Electrophysiol, 2:285-292 (1998).

Final Office Action; U.S. Appl. No. 12/827,700; Mailed on Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.

Gelfand, M., et al., "Treatment of renal failure and hypertension." U.S. Appl. No. 60/442,970, Jan. 29, 2003, 23 pages.

Gertner, Jon, "Meet the Tech Duo That's Revitalizing The Medical Device Industry." Fast Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hall, W. H., et al. "Combined embolization and percutaneous radiofrequency ablation of a solid renal tumor." *Am. J. Roentgenol*,174: 1592-1594 (2000).

Han, Y.-M, et al., "Renal artery ebolization with diluted hot contrast medium: An experimental study." J Vasc Intery Radiol, 12: 862-868 (2001).

Hansen, J. M., et al. "The transplanted human kidney does not achieve functional reinnervation." *Clin. Sci*, 87: 13-19 (1994).

Hendee, W. R. et al. "Use of Animals in Biomedical Research: The Challenge and Response." *American Medical Association White Paper* (1988) 39 pages.

Hering, Dagmara et al., "Chronic kidney disease: role of sympathetic nervous system activation and potential benefits of renal denervation." EuroIntervention, vol. 9, 2013, 9 pages.

Huang et al., "Renal denervation prevents and reverses hyperinsulinemia-induced hypertension in rats." Hypertension 32 (1998) pp. 249-254.

Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S.J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D.L.,et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Medical-Dictionary.com, Definition of "Animal Model," http://medical-dictionary.com (search "Animal Model"), 2005, 1 page.

Medtronic, Inc., Annual Report (Form 10-K) (Jun. 28, 2011) 44 pages.

Millard, F. C., et al, "Renal Embolization for ablation of function in renal failure and hypertension." Postgraduate Medical Journal, 65, 729-734, (1989).

Oliveira, V., et al., "Renal denervation normalizes pressure and baroreceptor reflex in high renin hypertension in conscious rats." Hypertension, 19:II-17-II-21 (1992).

Ong, K. L., et al. "Prevalence, Awareness, Treatment, and Control of Hypertension Among United States Adults 1999-2004." Hypertension, 49: 69-75 (2007) (originally published online Dec. 11, 2006).

Ormiston, John et al., "First-in-human use of the OneShot™ renal denervation system from Covidien." EuroIntervention, vol. 8, 2013, 4 pages.

Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.

Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

Peet, M., "Hypertension and its Surgical Treatment by bilateral supradiaphragmatic splanchnicectomy" Am J Surgery (1948) pp. 48-68.

(56) References Cited

OTHER PUBLICATIONS

Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Stouffer, G. A. et al., Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium rentention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Denervation in Patients with Resistant Hypertension." Journal of the American College of Cardiology, 2013, doi: 10.1016/j.jacc.2013.07.046, 24 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operators Manual of Boston Scientific's EPT-1000 XP Cardiac Ablation Controller & Accessories, Version of Apr. 2003, (6 pages).
Excerpt of Operators Manual of Boston Scientific's Maestro 30000 Cardiac Ablation System, Version of Oct. 17, 2005 , (4 pages).

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.

(56) References Cited

OTHER PUBLICATIONS

Krum, et al., "Renal Sympathetic-Nerve Ablation for Uncontrolled Hypertension." New England Journal of Med, Aug. 2009, 361;9.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

Mahfoud et al. "Treatment strategies for resistant arterial hypertension" Dtsch Arztebl Int. 2011;108:725-731.

Osborn, et al., "Effect of Renal Nerve Stimulation on Renal Blood Flow Autoregulation and Antinatriuresis During Reductions in Renal Perfusion Pressure," Proceedings of the Society for Experimentla Biology and Medicine, vol. 168, 77-81, 1981.

Page, I.H. et al., "The Effect of Renal Denervation on Patients Suffering From Nephritis," Feb. 27, 1935;443-458.

Page, I.H. et al., "The Effect of Renal Denervation on the Level of Arterial Blood Pressure and Renal Function in Essential Hypertension," J. Clin Invest. 1934;14:27-30.

Rocha-Singh, "Catheter-Based Sympathetic Renal Denervation," Endovascular Today, Aug. 2009.

Schlaich, M.P. et al., "Renal Denervation as a Therapeutic Approach for Hypertension: Novel Implictions for an Old Concept," Hypertension, 2009; 54:1195-1201.

Schlaich, M.P. et al., "Renal Sympathetic-Nerve Ablation for Uncontrolled Hypertension," N Engl J Med 2009; 361(9): 932-934.

Smithwick, R.H. et al., "Splanchnicectomy for Essential Hypertension," Journal Am Med Assn, 1953; 152:1501-1504.

Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.

Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.

United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

Valente, John F. et al., "Laparoscopic Renal Denervation for Intractable ADPKD-Related Pain", Nephrol Dial Transplant (2001) 16:160.

Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.

Beale et al., "Minimally Invasive Treatment for Varicose Veins: A Review of Endovenous Laser Treatment and Radiofrequency Ablation". Lower Extremity Wounds 3(4), 2004, 10 pages.

Chinushi et al., "Blood Pressure and Autonomic Responses to Electrical Stimulation of the Renal Arterial Nerves Before and After Ablation of the Renal Artery." Hypertension, 2013, 61, pp. 450-456.

Demosthenous, A. et al., "A Programmable ENG Amplifier with Passive EMG Neutralization for FES Application", Circuits and Systems, 2008, 4 pages.

Demosthenous, A. et al., "An Adaptive ENG Amplifier for Tripolar Cuff Electrodes", IEEE Journal of Solid-State Circuits, vol. 40, No. 2, Feb. 2005, 10 pages.

Doumas, Michael et al., "Renal Nerve Ablation for Resistant Hypertension: The Dust Has Not Yet Settled." The Journal of Clinical Hypertension. 2014; vol. 16, No. 6, 2 pages.

International Search Report and Written Opinion of International Application No. PCT/US2014/053205, mailed Nov. 13, 2014, 12 pages.

Messerli, Franz H. et al. "Renal Denervation for Resistant Hypertension: Dead or Alive?" Healio: Cardiology today's Intervention, May/Jun. 2014, 2 pages.

Miller, Reed, "Finding a Future for Renal Denervation With Better Controlled Trials." Pharma & Medtech Business Intelligence, Article # 01141006003, Oct. 6, 2014, 4 pages.

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.

Papademetriou, Vasilios et al., "Renal Nerve Ablation for Resistant Hypertension: How Did We Get Here, Present Status, and Future Directions." Circulation. 2014; 129: 1440-1450.

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Pokushalov et al., "A Randomized Comparison of Pulmonary Vein Isolation With Versus Without Concomitant Renal Artery Denervation in Patients With Refractory Symptomatic Atrial Fibrillation and Resistant Hypertension." Journal of the American College of Cardiology, 2012, 8 pages.

Pieper et al., "Design and Implementation of a New Computerized System for Intraoperative Cardiac Mapping." Journal of Applied Physiology, 1991, vol. 71, No. 4, pp. 1529-1539.

Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.

U.S. Appl. No. 60/852,787, filed Oct. 18, 2006, 112 pages.

\* cited by examiner

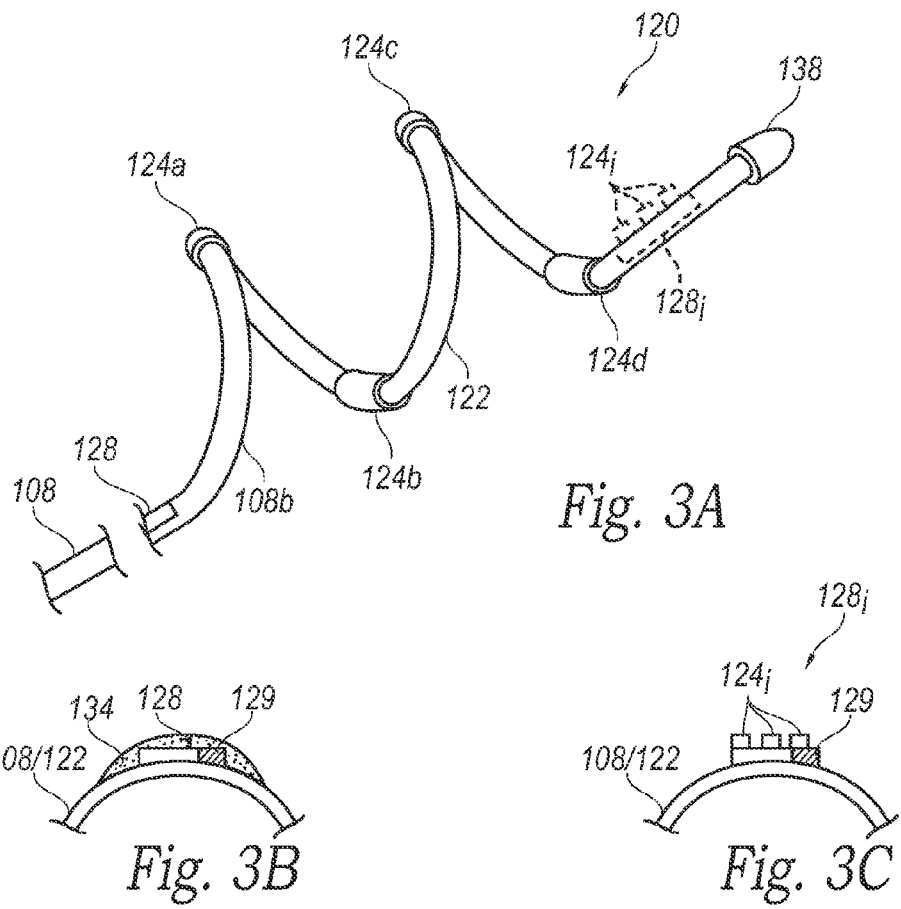
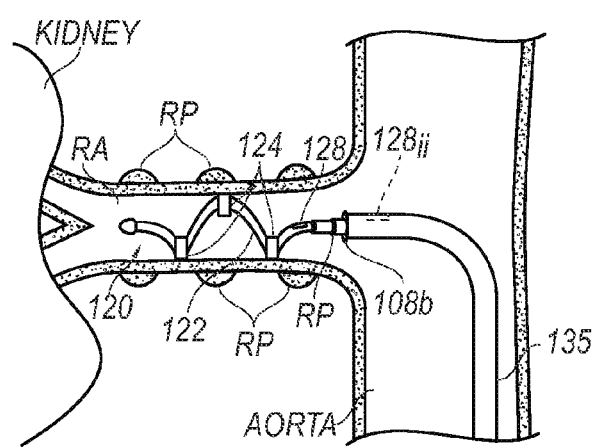
Fig. 3A
Fig. 3B
Fig. 3C
Fig. 3D

US 9,339,332 B2

NEUROMODULATION CATHETERS WITH NERVE MONITORING FEATURES FOR TRANSMITTING DIGITAL NEURAL SIGNALS AND ASSOCIATED SYSTEMS AND METHODS

TECHNICAL FIELD

The present technology is related to neuromodulation devices. In particular, at least some embodiments in accordance with the present technology are related to neuromodulation catheters having nerve monitoring features for transmitting digital neural signals.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIG. 3A is an enlarged isometric view of a distal portion of the neuromodulation catheter of FIG. 1 configured in accordance with an embodiment of the present technology.

FIG. 3B is an enlarged partial sectional view of a digitizer at the distal portion of the neuromodulation catheter of FIG. 3A configured in accordance with an embodiment of the present technology.

FIG. 3C is an enlarged partial sectional view of a digitizer at the distal portion of the neuromodulation catheter of FIG. 3A configured in accordance with another embodiment of the present technology.

FIG. 3D is a side view of the distal portion of the neuromodulation catheter of FIG. 3A within a blood vessel in accordance with an embodiment of the present technology.

DETAILED DESCRIPTION

Neuromodulation catheters configured in accordance with at least some embodiments of the present technology can include contacts that record neural signals before and/or after neuromodulation and a digitizer that digitizes the recorded neural signals and transmits the digitized neural signals to an extracorporeal device. Specific details of several embodiments of the present technology are described herein with reference to FIGS. 1-15B. Although many of the embodiments are described with respect to devices, systems, and methods for intravascular renal neuromodulation, other applications and other embodiments in addition to those described herein are within the scope of the present technology. For example, at least some embodiments may be useful for intraluminal neuromodulation, for extravascular neuromodulation, for non-renal neuromodulation, and/or for use in therapies other than neuromodulation. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation device). The terms, "distal" and "distally" refer to a position distant from or in a direction away from a clinician or a clinician's control device. The terms "proximal" and "proximally" refer to a position near or in a direction toward a clinician or a clinician's control device. The headings provided herein are for convenience only and should not be construed as limiting the subject matter disclosed.

I. SELECTED EXAMPLES OF NEUROMODULATION DEVICES AND RELATED SYSTEMS

Figure 1:
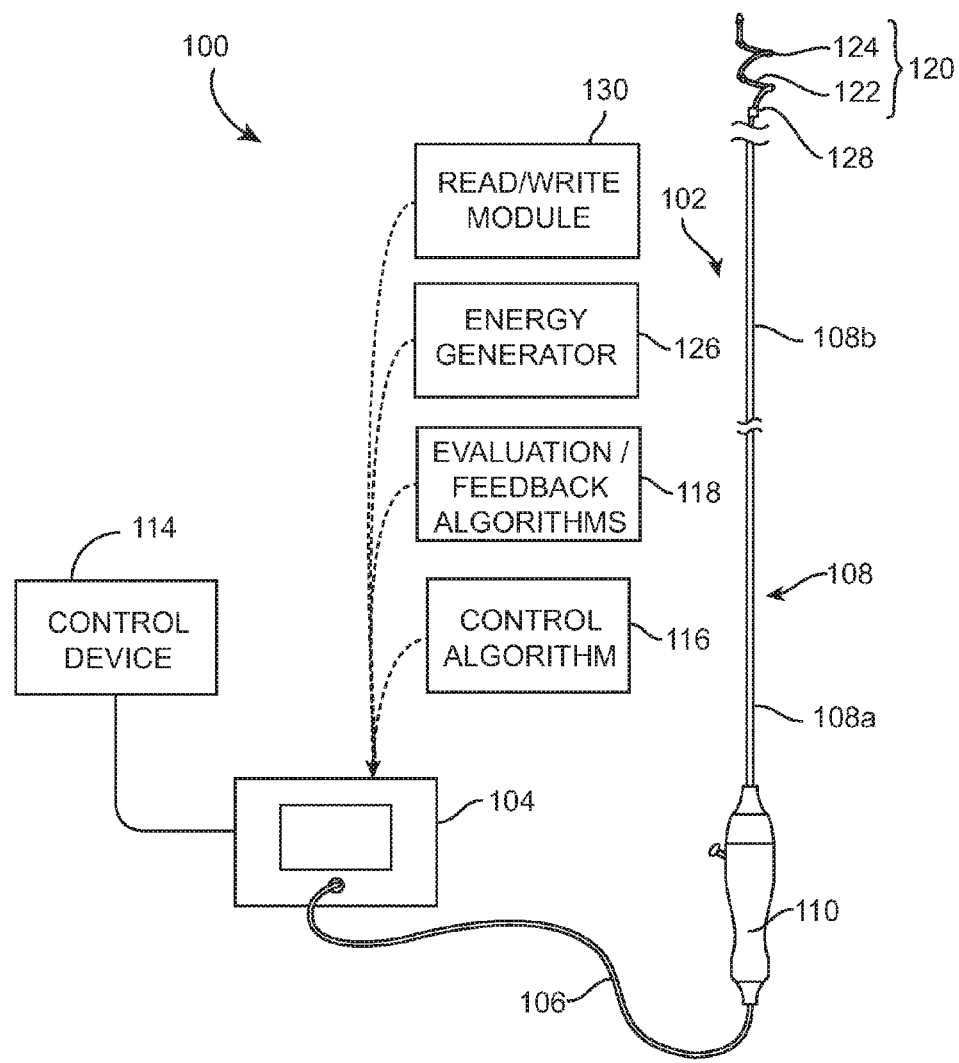
FIG. 1 is a partially schematic illustration of a neuromodulation system including a neuromodulation catheter configured in accordance with an embodiment of the present technology.

FIG. 1 is a partially schematic illustration of a therapeutic system 100 ("system 100") configured in accordance with an embodiment of the present technology. The system 100 can include a neuromodulation catheter 102, a console 104, and a cable 106 extending therebetween. The neuromodulation catheter 102 can include an elongated shaft 108 having a proximal portion 108a, a distal portion 108b, a handle 110 operably connected to the shaft 108 at the proximal portion 108a, and a neuromodulation assembly 120 operably connected to the shaft 108 at the distal portion 108b. The shaft 108 and the neuromodulation assembly 120 can be 2, 3, 4, 5, 6, or 7 French or one or more other suitable sizes. As shown in FIG. 1, the neuromodulation assembly 120 can include a support structure 122 carrying an array of two or more contacts 124 and a digitizer 128. The contacts 124 can be configured to detect analog neural signals, and the digitizer 128 can be configured to digitize the analog neural signals and transmit the digitized neural signals to an extracorporeal device. In certain embodiments, the contacts 124 can be energy delivery elements, such as electrodes, that not only record neural signals, but also delivery energy (e.g., RF energy) to a target site within a body lumen to provide neuromodulation treatment at the target site. In other embodiments, the digitizer 128 itself can include contacts that measure analog neural signals at the target site, and the contacts 124 along the support structure 122 can be dedicated to energy delivery. As described in further detail below, in further embodiments the contacts 124 can be dedicated to neural recording, and the neuromodulation assembly 120 can include other types of energy delivery elements that provide neuromodulation treatment using various modalities, such as cryotherapeutic cooling, ultrasound radiation, etc.

The distal portion 108b of the shaft 108 can be configured to be moved within a lumen of a human patient and locate the neuromodulation assembly 120 at a target site within or otherwise proximate to the lumen. For example, shaft 108 can be configured to position the neuromodulation assembly 120 within a blood vessel, a duct, an airway, or another naturally occurring lumen within the human body. In certain embodiments, intravascular delivery of the neuromodulation assembly 120 includes percutaneously inserting a guide wire (not shown) into a body lumen of a patient and moving the shaft 108 and/or the neuromodulation assembly 120 along the guide wire until the neuromodulation assembly 120 reaches a target site (e.g., a renal artery). For example, the distal end of the neuromodulation assembly 120 may define a passageway for engaging the guide wire for delivery of the neuromodulation assembly 120 using over-the-wire (OTW) or rapid exchange (RX) techniques. In other embodiments, the neuromodulation catheter 102 can be a steerable or non-steerable device configured for use without a guide wire. In still other embodiments, the neuromodulation catheter 102 can be configured for delivery via a guide catheter or sheath (not shown).

Once at the target site, the neuromodulation assembly 120 can be configured to detect neural signals by recording electrical activity of neurons proximate to the target site using the contacts 124 along the support member 122 and/or contacts integrated into the digitizer 128. The digitizer 128 can be configured to receive analog neural signals from the contacts 124, digitize the analog neural signals into digital neural signals, and transmit the digital neural signals to a read/write module 130 (shown schematically) and/or other device external to the patient. The read/write module 130 can be configured to receive and store the digital neural signals for further use by a clinician or operator. For example, a clinician can use the neural information received by the read/write module 130 to monitor neural activity before, during, and/or after neuromodulation treatment and/or compile data related to neural activity for future use. In the embodiment illustrated in FIG. 1, the read/write module 130 is integrated into the console 104 with other features of the system 100. In other embodiments, however, the read/write module 130 can be a separate component and/or part of another device (e.g., a computer) communicatively coupled to the digitizer 128. As explained in further detail below, these digitized neural signals can be used to make various determinations related to the nerves proximate to the target site, such as whether a neuromodulation treatment was effective in ablating the nerves at the target site.

The digitizer 128 can communicate with the read/write module 130 via electrical wires that run through or along the shaft 108 and the cable 106, or via a telemetry module or other type of communication device that wirelessly transmits digitized neural signals to a receiver of the read/write module 130. For example, the digitizer 128 can be inductively coupled to the read/write module 130. In certain embodiments, the digitizer 128 can further be configured to filter or otherwise process the analog signals to differentiate electroneurogram (ENG) signals from electromyogram (EMG) signals and/or other background noise in the recorded signal before digitizing the analog signals. The digitizer 128 can thus capture, filter, and digitize the analog neural signals proximate to the site at which they are recorded, rather than transmitting the recorded analog neural signals through long signal wires that may attenuate or otherwise alter the analog signals. Accordingly, the system 100 is expected to reduce the likelihood of measurement errors or other distortion in the ENG signals.

Before and/or after detecting the neural signals, the neuromodulation assembly 120 can provide or facilitate neuromodulation treatment at the target site using the contacts 124 and/or other energy delivery elements. For example, the contacts 124 can facilitate RF ablation of nerves proximate to the target site. In other embodiments, the neuromodulation assembly 120 can deliver neuromodulation energy to nerves proximate to the target site using various other modalities, such as cryotherapeutic cooling, ultrasonic radiation, etc. The digitizer 128 can detect neural signals after energy delivery to provide an operator with real-time feedback as to the effectiveness of the neuromodulation treatment.

The console 104 can be configured to control, monitor, supply, and/or otherwise support operation of the neuromodulation catheter 102. The console 104 can further be configured to generate a selected form and/or magnitude of energy for delivery to tissue at the target site via the neuromodulation assembly 120, and therefore the console 104 may have different configurations depending on the treatment modality of the neuromodulation catheter 102. For example, when the neuromodulation catheter 102 is configured for electrode-based, heat-element-based, or transducer-based treatment, the console 104 can include an energy generator 126 (shown schematically) configured to generate radio frequency (RF) energy (e.g., monopolar and/or bipolar RF energy), pulsed energy, microwave energy, optical energy, ultrasound energy (e.g., intravascularly delivered ultrasound, extracorporeal ultrasound, and/or high-intensity focused ultrasound (HIFU)), direct heat energy, radiation (e g, infrared, visible, and/or gamma radiation), and/or another suitable type of energy. When the neuromodulation catheter 102 is configured for cryotherapeutic treatment, the console 104 can include a refrigerant reservoir (not shown), and can be configured to supply the neuromodulation catheter 102 with refrigerant. Similarly, when the neuromodulation catheter 102 is configured for chemical-based treatment (e.g., drug infusion), the console 104 can include a chemical reservoir (not shown) and can be configured to supply the neuromodulation catheter 102 with one or more chemicals.

In selected embodiments, the system 100 may be configured to deliver a monopolar electric field via one or more of the contacts 124. In such embodiments, a neutral or dispersive electrode 130 (FIG. 2) may be electrically connected to the generator 126 and attached to the exterior of the patient. In embodiments including multiple contacts 124, the contacts 124 may deliver power independently (i.e., may be used in a monopolar fashion), either simultaneously, selectively, or sequentially, and/or may deliver power between any desired combination of the contacts 124 (i.e., may be used in a bipolar fashion). In addition, an operator optionally may be permitted to choose which contacts 124 are used for power delivery in order to form highly customized lesion(s) within the renal artery, as desired. One or more sensors (not shown), such as one or more temperature (e.g., thermocouple, thermistor, etc.), impedance, pressure, optical, flow, chemical, and/or other sensors, may be located proximate to, within, or integral with the contacts 124. The sensor(s) and the contacts 124 can be connected to one or more supply wires (not shown) that transmit signals from the sensor(s) and/or convey energy to the contacts 124.

In various embodiments, the system 100 can further include a control device 114 communicatively coupled to the neuromodulation catheter 102. The control device 114 can be configured to initiate, terminate, and/or adjust operation of one or more components (e.g., the contacts 124) of the neuromodulation catheter 102 directly and/or via the console 104. In other embodiments, the control device 114 can be omitted or have other suitable locations (e.g., within the handle 110, along the cable 106, etc.). The console 104 can be configured to execute an automated control algorithm 116 and/or to receive control instructions from an operator. Further, the console 104 can be configured to provide feedback to an operator before, during, and/or after a treatment procedure via an evaluation/feedback algorithm 118.

Figure 2:
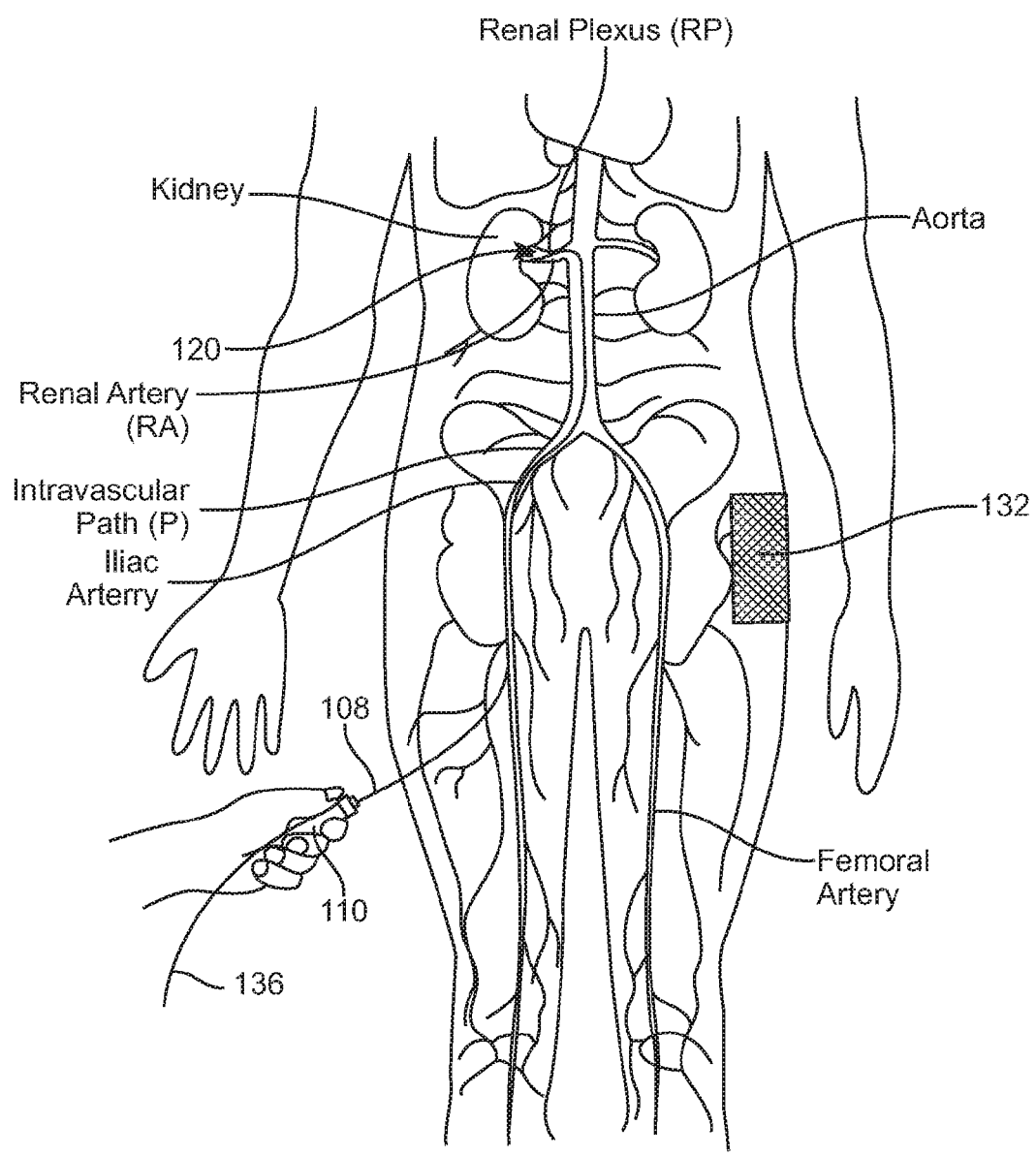
FIG. 2 illustrates monitoring and/or modulating renal nerves with the neuromodulation catheter of FIG. 1 in accordance with an embodiment of the present technology.

FIG. 2 (with additional reference to FIG. 1) illustrates modulating renal nerves in accordance with an embodiment of the system 100. The neuromodulation catheter 102 provides access to the renal plexus RP through an intravascular path P, such as a percutaneous access site in the femoral (illustrated), brachial, radial, or axillary artery to a targeted treatment site within a respective renal artery RA. By manipulating the proximal portion 108a of the shaft 108 from outside the intravascular path P, a clinician may advance the shaft 108 through the sometimes tortuous intravascular path P and remotely manipulate the distal portion 108b (FIG. 1) of the shaft 108. In the embodiment illustrated in FIG. 2, the neuromodulation assembly 120 is delivered intravascularly to the treatment site using a guide wire 136 in an OTW technique. As noted previously, the distal end of the neuromodulation assembly 120 may define a passageway for receiving the guide wire 136 for delivery of the neuromodulation catheter 102 using either OTW or RX techniques. At the treatment site, the guide wire 136 can be at least partially withdrawn or removed, and the neuromodulation assembly 120 can transform or otherwise be moved to a deployed arrangement for recording neural activity and/or delivering energy at the treatment site. In other embodiments, the neuromodulation assembly 120 may be delivered to the treatment site within a guide sheath (not shown) with or without using the guide wire 136. When the neuromodulation assembly 120 is at the target site, the guide sheath may be at least partially withdrawn or refracted and the neuromodulation assembly 120 can be transformed into the deployed arrangement. As described in further detail below, in certain embodiments the digitizer 128 (FIG. 1) can be carried by the guide sheath and communicatively coupled to the contacts 124 (FIG. 1). In still other embodiments, the shaft 108 may be steerable itself such that the neuromodulation assembly 120 may be delivered to the treatment site without the aid of the guide wire 136 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation assembly 120. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the neuromodulation assembly 120. Further, in some embodiments, image guidance components (e.g., IVUS, OCT) may be integrated with the neuromodulation catheter 102 and/or run in parallel with the neuromodulation catheter 102 to provide image guidance during positioning of the neuromodulation assembly 120. For example, image guidance components (e.g., IVUS or OCT) can be coupled to the neuromodulation assembly 120 to provide three-dimensional images of the vasculature proximate the target site to facilitate positioning or deploying the multi-electrode assembly within the target renal blood vessel.

Energy from the contacts 124 (FIG. 1) and/or other energy delivery elements may then be applied to target tissue to induce one or more desired neuromodulating effects on localized regions of the renal artery RA and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery elements and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

Hypothermic effects may also provide neuromodulation. For example, a cryotherapeutic applicator may be used to cool tissue at a target site to provide therapeutically-effective direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Embodiments of the present technology can include cooling a structure at or near an inner surface of a renal artery wall such that proximate (e.g., adjacent) tissue is effectively cooled to a depth where sympathetic renal nerves reside. For example, the cooling structure is cooled to the extent that it causes therapeutically effective, cryogenic renal-nerve modulation. Sufficiently cooling at least a portion of a sympathetic renal nerve is expected to slow or potentially block conduction of neural signals to produce a prolonged or permanent reduction in renal sympathetic activity.

The contacts 124 on the neuromodulation assembly 120 can intravascularly detect electrical signals before and/or after neuromodulation energy is applied to the renal artery RA. This information can then be filtered or otherwise processed by the digitizer 128 (FIG. 1) to differentiate the neural activity from other electrical signals (e.g., smooth cell/muscle signals), and the resultant ENG signals can be digitized and transmitted to the read/write module 130 (FIG. 1). In other embodiments, the digitizer 128 simply digitizes the recorded analog signals and the digitized signals are processed at an extracorporeal device, such as the read/write module 130 (FIG. 1). Since the digitizer 128 digitizes the analog neural signals proximate to the site at which they are recorded, the neuromodulation catheter 102 can reduce the likelihood that the recorded analog signals are attenuated or otherwise altered as they may be while traveling through signal wires. The digitized ENG signals can be used to determine whether the neuromodulation treatment was effective. For example, statistically meaningful decreases in the ENG signal(s) taken after neuromodulation can serve as an indicator that the nerves were sufficiently ablated. Statistically meaningful decreases or drops in ENG signals generally refers to measureable or noticeable decreases in the ENG signals.

II. SELECTED EMBODIMENTS OF NERVE MONITORING ASSEMBLIES AND NEUROMODULATION ASSEMBLIES

FIG. 3A is an enlarged isometric view of the neuromodulation assembly 120 of the neuromodulation catheter 102 of FIG. 1 configured in accordance with an embodiment of the present technology, and FIGS. 3B and 3C are an enlarged partial sectional view of digitizers 128 and $128_t$, respectively, carried by the neuromodulation assembly 120 of FIG. 3A. As shown in FIG. 3A, the neuromodulation assembly 120 can include an array of four contacts 124 (identified individually as first through fourth contacts 124a-d, respectively), the digitizer 128, and the support member 122 carrying the contacts 124 and the digitizer 128. In other embodiments the neuromodulation assembly may include a different number of contacts 124 (e.g., 1, 2, 8, 12, etc. contacts 124) and/or more than one digitizer 128 arranged along the length of the support member 122.

The support member 122 can be made from various different types of materials (e.g., metals and/or polymers) suitable for supporting the contacts 124 and the digitizer 128. In the illustrated embodiment, the support member 122 has a helical shape in the deployed state. The dimensions (e.g., outer diameter and length) of the helical support member 122 can be selected to accommodate the vessels or other body lumens in which the neuromodulation assembly 120 is designed to be delivered. For example, the axial length of the deployed support member 122 may be selected to be no longer than a patient's renal artery (e.g., typically less than 7 cm), and have a diameter that accommodates the inner diameter of a typical renal artery (e.g., about 2-10 mm). In other embodiments, the support member 122 can have other dimensions depending on the body lumen within which it is configured to be deployed. In further embodiments, the support member 122 can have other suitable shapes (e.g., semi-circular, curved, straight, etc.), and/or the neuromodulation assembly 120 can include multiple support members 122 configured to carry one or more contacts 124 and/or one or more digitizers 128. The support member 122 may be designed to apply a desired outward radial force to a vessel when expanded to a deployed state (shown in FIG. 1) to place the contact 124 in contact with the inner surface of the vessel wall. For example, FIG. 3D illustrates the support member 122 in a deployed state pressing the contacts 124 against the interior wall of a renal artery RA. In embodiments where the digitizer 128 includes contacts and/or electrodes, the support member 122 can be configured to press the digitizer 128 against the wall of the renal artery RA.

As shown in FIG. 3A, the support member 122 can optionally terminate with an atraumatic (e.g., rounded) tip 138. The atraumatic tip 138 may reduce the risk of injuring the blood vessel as the helically-shaped support member 122 expands and/or as a delivery sheath is refracted from the neuromodulation assembly 120. The atraumatic tip 138 can be made from a polymer or metal that is fixed to the end of the structural element by adhesive, welding, crimping, over-molding, solder, and/or other suitable attachment mechanisms. In other embodiments, the atraumatic tip 138 may be made from the same material as the support member 122, and integrally formed therefrom (e.g., by machining or melting). In further embodiments, the distal end portion of the support member 122 may have a different configuration and/or features. For example, in some embodiments the tip 138 may comprise a contact, an energy delivery element, a digitizer, and/or a radiopaque marker.

As discussed above, the contacts 124 can be configured to detect analog electrical signals at a target site within a body lumen, and the digitizer 128 can be configured to receive the analog electrical signals to provide digitized ENG signals to an extracorporeal receiver, such as, the read/write module 130 of FIG. 1. In various embodiments, pairs of the contact 124 can be configured to provide multi-polar (e.g., bipolar)

recording of electrical activity proximate to a target site in a vessel. The contacts 124 can be arranged in various different pairs to detect electrical activity from different longitudinal segments and/or other portions of the vessel. For example, the first contact 124a can be paired with any one of the second contact 124b, the third contact 124c, or the fourth contact 124d. In other embodiments, other contacts 124 can be paired with each other depending on the number of contacts 124 on the neuromodulation assembly 120 and/or the arrangement of the contacts 124 along the support member 122. Multi-polar recording of neural activity is expected to reduce noise that would otherwise be collected via a single contact because, as described in further detail below, differential amplification of multi-polar recordings provided by the digitizer 128 can selectively amplify the difference in the signals (e.g., the nerve action potential, i.e., the electrical potential developed in a nerve cell during cellular activity), while suppressing the common signals (e.g., the background noise and EMG signals).

In certain embodiments, the neural recordings taken from a first pair of contacts 124 can be compared with neural recordings taken from one or more other pairs of contacts 124. For example, the neural recordings taken from a first electrode pair consisting of the first and second contacts 124a and 124b can be compared with the neural recordings taken from electrode pairs consisting of the first and third contacts 124a and 124c and/or the first and fourth contacts 124a and 124d. In further examples, the neural recordings taken from the first and second contacts 124a and 124b can be compared with those taken from the third and fourth contacts 124c and 124d, and/or the neural recordings taken from the second and third contacts 124b and 124c can be compared with those taken from the third and fourth contacts 124c and 124d. In embodiments including more or less than four contacts 124, neural recordings taken from different electrode pairs can be compared with each other. Comparing the different neural recordings can provide a more complete understanding of the neural activity before and/or after therapeutic energy delivery, such as whether neuromodulation was more effective along a certain longitudinal segment of a vessel. The comparison of neural recordings taken from different electrode pairs can also determine if certain electrode pairs detect stronger, more consistent, or otherwise better neural signals than other electrode pairs. In other embodiments, the individual contacts 124 can record neural activity in a monopolar fashion.

The analog electrical activity recorded by the contacts 124 can be transmitted to the digitizer 128. For example, the contacts 124 can be electrically coupled to the digitizer 128 via signal wires (not shown; e.g., copper wires) extending from the contacts 124 through or along the support member 122 and/or the shaft 108 to the digitizer 128. In other embodiments, the digitizer 128 can be communicatively coupled to contacts 124 using other communication means, such as wireless coupling. In the embodiment illustrated in FIG. 3A, the digitizer 128 is positioned along the support member 122 of the neuromodulation assembly 120 proximal to the contacts 124. As further shown in FIG. 3A, a digitizer $128_i$ (shown in broken lines) can also or alternatively be positioned distal to the contacts 124 along the support member 122. In other embodiments, the digitizer 128 can be spaced between the contacts 124, or positioned elsewhere along the neuromodulation assembly 120. In further embodiments, the neuromodulation assembly 120 can include more than one digitizer 128. For example, multiple digitizers can be positioned along the length of the support member 122.

As shown in FIG. 3B, the digitizer 128 can be a small chip (e.g., a microchip) that is carried by an outer surface of the support member 122 or the shaft 108 and covered by a protective encapsulant 134. The digitizer chip can have a cross-sectional dimension of about 3×3 mm to about 5×5 mm, or may have smaller or larger dimensions. In other embodiments, the digitizer 128 can be positioned within the support member 122 or the shaft 108. In further embodiments, the digitizer 128 can be positioned on or in other portions of the neuromodulation assembly 120, other portions of the neuromodulation catheter 102 (FIG. 1), and/or other portions of the system 100 (FIG. 1). The digitizer 128 can be configured to receive the analog neural signals from the contacts 124, digitize the analog neural signals into digital neural signals, and transmit the digital neural signals to an extracorporeal device (e.g., the read/write module 130 of FIG. 1). For example, the digitizer 128 can include an analog to digital circuit that converts the recorded signals into digital signals. In various embodiments, the digitizer 128 can further be configured to filter the analog signals received from the contacts 124 to differentiate neural signals (e.g., ENG signals) from EMG signals and other background noise before digitizing the analog neural signals. For example, the digitizer 128 can include one or more of the amplifier assemblies described below with reference to FIGS. 4A-4C to at least substantially remove EMG and other signals from the analog neural signals. In other embodiments, the recorded neural signals can be filtered or otherwise processed after being digitized, such as at an extracorporeal device.

The digitizers 128 can be communicatively coupled to the read/write module 130 (FIG. 1) and/or another extracorporeal module by signal wires (not shown) that extend from the digitizer 128 to the read/write module 130. For example, when the digitizer 128 is positioned at the neuromodulation assembly 120 and the read/write module 130 is incorporated into the console 104 (FIG. 1), the signal wires can extend through or along the shaft 108 and the cable 106 (FIG. 1) to the read/write module 130. In other embodiments, the signal wires can extend along different lengths of shaft 108 depending upon the location of the digitizer 128 and the read/write module 130.

In further embodiments, the digitizer 128 can be wirelessly coupled to the read/write module 130 rather than hardwired thereto. As shown in FIG. 3B, for example, the digitizer 128 can include a telemetry module or system 129 that can wirelessly transmit the digitized neural signals from within a human patient to the read/write module 130. The extracorporeal read/write module 130 can be inductively coupled to the digitizer 128. In other embodiments, the telemetry module 129 can wirelessly couple the digitizer 128 to the read/write module 130 using other suitable wireless communication means, such as radio waves, computer systems, etc. In further embodiments, the telemetry module 129 and the digitizer 128 can be separate components communicatively coupled to each other.

FIG. 3C illustrates a digitizer $128_i$ configured in accordance with another embodiment of the present technology. The digitizer $128_i$ can include several features generally similar to the features of the digitizer 128 of FIG. 3B. For example, the digitizer $128_i$ can include an analog to digital circuit that converts analog signals received from contacts to digital signals, an amplifier assembly and/or other processing circuit that distinguishes ENG signals from EMG signals and other background noise, and an optional telemetry module 129 that wirelessly couples the digitizer $128_i$ to the read/write module 130 (FIG. 1). As shown in FIG. 3C, the digitizer $128_i$ can further include a plurality of contacts $124_i$ (e.g., 2, 3, 4, or more electrodes) configured to detect electrical activity proximate to a treatment site within a vessel or other body lumen. The support member 122 can be configured to place the contacts $124_i$ integrated with the digitizer $128_i$ into contact with the vessel wall to allow the contacts $124_i$ to adequately measure electrical activity. Accordingly, instead of using the contacts 124 (FIG. 3A) to record neural activity, the digitizer $128_i$ of FIG. 3C has dedicated measurement contacts $124_i$ that detect the electrical activity that is subsequently filtered and digitized. In selected embodiments, the contacts $124_i$ of the digitizer $128_i$ can also be configured to deliver therapeutic and/or non-therapeutic levels of energy to a target site. In certain embodiments, the neuromodulation assembly 120 (FIG. 3A) can include more than one digitizer $128_i$ spaced along the length of the support member 122 to record neural activity from various different portions along a vessel. For example, digitizers $128_i$ can be positioned adjacent to each of the contacts 124 along the support member 122, or the contacts 124 can be replaced by the digitizers 128. In embodiments including multiple digitizers $128_i$ with telemetry modules 129, the read/write module 130 (FIG. 1) can be multiplexed to receive digitized neural signals from the various digitizers 128.

As shown in FIG. 3D, in another embodiment a digitizer $128_{ii}$ can be positioned on a distal portion of a guide sheath or guide catheter 135. In this embodiment, the contacts 124 along the support member 122 can be configured to record neural activity, and the digitizer $128_{ii}$ can be communicatively coupled to the contacts 124. For example, the neuromodulation assembly 120 can include one or more transmitters (not shown), telemetry modules, and/or other types of communication devices communicatively coupled to the contacts 124, and the communication device can wirelessly transmit the recorded analog electrical signals from the contacts 124 to the digitizer $128_{ii}$ on the guide catheter 135. Similar to the digitizer 128 of FIG. 3B, the digitizer $128_{ii}$ on the guide catheter 135 can filter and digitize analog neural signals received from the contacts 124, and transmit digitized neural signals to an extracorporeal device. For example, the digitizer $128_{ii}$ can include a telemetry module integrated with or otherwise communicatively coupled to the digitizer $128_{ii}$ to transmit the digitized neural signals to the extracorporeal device.

In various embodiments, the contacts 124 can be configured to deliver energy to nerves proximate to a treatment site in a blood vessel or other body lumen. For example, the contacts 124 can be electrodes that deliver therapeutic levels of RF energy and/or other forms of electrical energy to nerves proximate to the target site. Each electrode can be operatively coupled to one or more signal wires (not shown; e.g., copper wires) that extend along the body of the shaft 108 to a proximal end of the shaft 108 where the signal wires can be operatively connected to an extracorporeal generator (e.g., the generator 126 of FIG. 1) to drive therapeutic energy delivery. In other embodiments, the telemetry module 129 and/or other communication device can wirelessly couple the electrodes to the generator. The electrodes can be configured to deliver bipolar energy to the nerves and/or deliver energy in a monopolar fashion. As described in further detail below, in other embodiments the neuromodulation assembly 120 can have other suitable energy delivery elements for delivering various forms of energy to the target site, such as ultrasound transducers, radiation emitters, cryotherapeutic applicators, and/or other energy delivery elements.

In operation, the neuromodulation assembly 120 can be intravascularly delivered to a target site within a blood vessel or other body lumen, and the neuromodulation assembly 120 can be deployed to place the contacts 124 and, in some embodiments, the digitizer 128, against the interior wall of the blood vessel. In certain embodiments, one or more of the contacts 124 along the support member 122 can record electrical activity from the nerves proximate to the vessel wall, and in other embodiments contacts $124_i$ integrated with the digitizer 128 can perform the recording function. The neural activity can be recorded from the nerves at their natural state and/or after applying nontherapeutic and/or therapeutic levels of stimulation. The digitizer 128 can distinguish neural signals (e.g., ENG signals) from other signals in the recorded electrical activity and digitize the analog neural signals. This information can be transmitted to the extracorporeal read/write module 130 (FIG. 1) wirelessly via the telemetry module 129 or via signal wires extending through the shaft 108. Because the analog neural signals are digitized proximate to where they are recorded, it is expected that the neural signals received at the read/write module 130 are not subject to as much degradation as they would if the analog neural signals had been transmitted through signal wires extending from the contacts 124 to the read/write module 130. Accordingly, the neuromodulation assembly 120 with the digitizer 128 positioned on or proximate thereto is expected to reduce the likelihood of measurement errors, which can be of particular importance when recording small neural signals that can be on the order of micro volts (μV).

The digitized neural signals can provide a baseline or reference ENG signal for determining whether subsequent neuromodulation is sufficient to provide a therapeutic effect. In certain embodiments, the neuromodulation assembly 120 can be moved proximally or distally along the length of the vessel to record neural signals at a plurality of locations along the vessel, and the recorded neural signals can be analyzed using various different decision metrics to determine a baseline ENG signal. For example, the recorded signals can be analyzed by integrating the recorded neural signals, omitting some recorded signals from consideration (e.g., when the recording appears abnormal or insufficient for consideration), averaging a plurality of the recorded neural signals (e.g., if they are similar), and/or weighting averages of the recorded signals to provide the baseline ENG signal. In one embodiment, for example, recordings can be taken from a plurality of electrode pairs (e.g., the first and second electrodes, the first and third electrodes, the first and fourth electrodes, the second and third electrodes, etc.), and compared with one another. If any of the electrode pairs record a signal that differs to a certain degree (e.g., a threshold percentage) from the signals recorded by the other electrode pairs, the outlier recordings can be discarded and the remaining recordings can be averaged or otherwise analyzed to determine the ENG signal. In other embodiments, neural recordings are taken from different electrode pairs, and the clearest signal is selected as the baseline ENG signal.

When the recorded ENG signals alone are insufficient to adequately measure the baseline neural activity, one or more of the contacts 124 can be used to stimulate nerves proximate to the treatment site at non-therapeutic energy levels, and one or more of the other contacts 124 can be configured to record the resultant neural activity of the modulated nerves. For example, the generator 126 (FIG. 1) can send a stimulating pulse to the first contact 124a, which in turn applies non-therapeutic levels of RF energy or another form of energy to a vessel wall sufficient to stimulate the nerves proximate to the vessel wall, and the second and third contacts 124b and 124c can record the resultant neural activity (e.g., the action potentials of the nerves) during or after delivery of the energy from the first contact 124a. In embodiments in which contacts $124_i$ are integrated with the digitizer 128, the external read/write module 130 (FIG. 1) can communicate with the digitizer 128 (e.g., via the telemetry modulate 129) to send a stimulating pulse to the contacts 124$_i$, and the same contacts 124$_i$ and/or contacts 124, 124$_i$ along the support member 122 can record the resultant neural activity.

In certain embodiments, the contacts 124 that were used to record nerve activity can subsequently be used to apply therapeutically-effective levels of energy (e.g., RF energy) to the vessel wall to modulate (e.g., ablate) the nerves proximate to the vessel wall. For example, if the recorded neural activity indicates nerve activity is above a desired threshold, the same contacts 124 used to record the neural activity can be used to ablate the nerves without the operator moving the contacts 124. The energy can be delivered from an energy generator (e.g., the energy generator of FIG. 1) via signal wires extending through the shaft 108 and/or via the telemetry module 129. In other embodiments, selected contacts 124 or other contacts can be designated solely for recording, and other contacts can be designated for therapeutic energy delivery. In further embodiments, the neuromodulation assembly 120 can include other energy delivery elements, such as radiation emitters, ultrasound transducers, and/or cryotherapeutic applicators, that apply therapeutically-effective levels of energy to the target site.

After applying the neuromodulation energy, one or more of the contacts 124, 124$_i$ along the support member 122 and/or integrated into the digitizer 128 can be used to record analog neural signals from within the vessel. The analog neural signals can again be filtered and digitized by the digitizer 128, and transmitted to the read/write module 130 (FIG. 1). As discussed above, ENG signals can optionally be taken from recordings at multiple locations within the vessel by moving the neuromodulation assembly 120 along the length of the vessel and/or recording neural activity from different pairs of contacts 124. These recording methods may provide the clinician a better understanding of the efficacy of the neuromodulation along the length of the vessel. The ENG signals taken before and after energy application can be compared to determine the effects of the neuromodulation. For example, decreases in the ENG signal (compared to the baseline ENG signal) may indicate therapeutically effective neuromodulation of the target nerves. The degree of the decrease may be used as an indicator of the efficacy of the neuromodulation. A lack of an ENG signal after neuromodulation may be indicative of complete denervation of the nerves extending proximate to the vessel. Increases in the ENG signal may indicate that sufficient ablation was not achieved, or other factors unrelated to the ablation energy may cause increases in the ENG signal. If the recorded readings from the nerves indicate that the nerves were not modulated to the desired extent, the same contacts 124 can be used to reapply therapeutically-effective levels of energy to the vessel wall to modulate the nerves proximate to the vessel wall. In certain embodiments, the operator can move the neuromodulation assembly 120 longitudinally and/or rotate the neuromodulation assembly 120 to apply the therapeutic energy to nerves along different portions of the vessel.

Figure 4A:
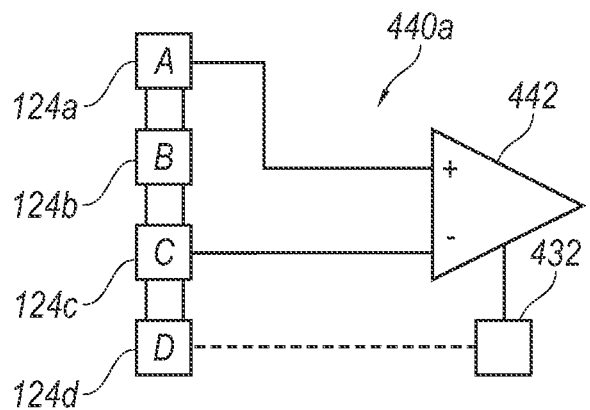
FIGS. 4A-4C are circuit diagrams of amplifier assemblies arranged in quasi-tripole (QT), true-tripole (TT), and adaptive or automatic tripole (AT) configurations, respectively, in accordance with embodiments of the present technology.
Figure 4B:
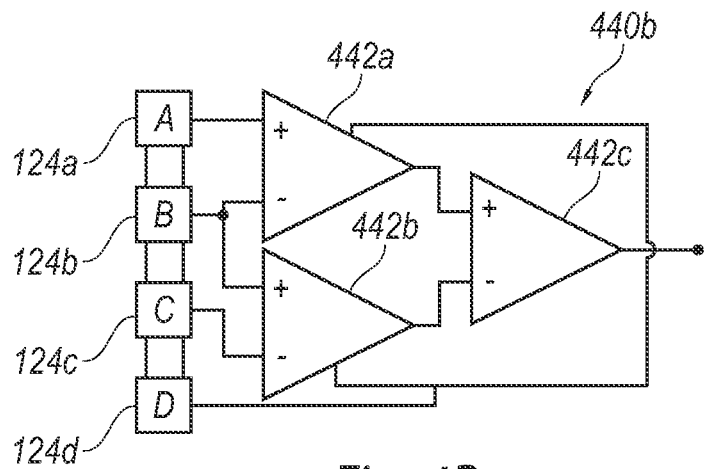
Figure 4C:
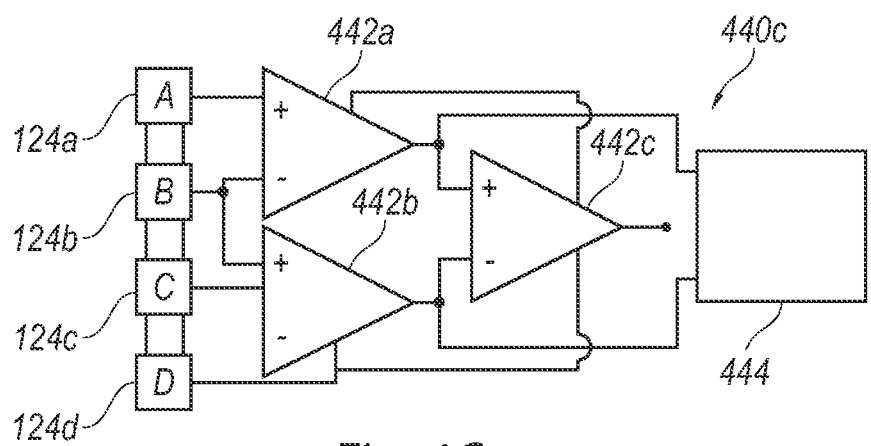

ENG recordings, which are typically on the order of micro volts (µV), may be obscured by interference from other signals that are typically generated from the muscles nearby (EMG signals on the order of several millivolts (mV)). However, as discussed above, the digitizer 128 can filter or otherwise process the signals recorded at the contacts 124, 124$_i$ to at least substantially remove EMG signals or other signals from nearby muscles and/or other background noise that interferes with the ENG signals. FIGS. 4A-4C, for example, illustrate circuit diagrams of various amplifier assemblies (identified individually as first through third amplifier assemblies 440a-c, respectively, and referred to collectively as amplifier assemblies 440) for detecting the ENG signals from the recordings taken at the contacts 124. The contacts 124 referred to below and shown in FIGS. 4A-4C can correspond to contacts integrated with a digitizer (e.g., the digitizer 128$_i$ of FIG. 3C) and/or separate from the digitizer (e.g., the digitizer 128 of FIG. 3B).

Referring to the embodiment illustrated in FIG. 4A, the first amplifier assembly 440a is arranged in a QT circuit in which two contacts 124 (e.g., the first and third contacts 124a and 124c) are electrically coupled to a differential amplifier 442. In other embodiments, a different pair of contacts 124 (e.g., the third and fourth contacts 124c and 124d) can be electrically coupled to the differential amplifier 442. The differential amplifier 442 can amplify the difference between the two contacts 124 connected thereto and, in doing so, is expected to at least substantially cancel out (e.g., minimize) EMG signals and other background noise common between the two contacts 124. The extent to which the QT amplifier assembly 440a can remove EMG signals depends at least in part on the contacts 124 being positioned symmetrically with respect to the vessel and the uniformity of the tissue (e.g., in thickness and consistency) in contact with the contacts 124. Two contacts (e.g., the second and fourth contacts 124b and 124d) can be shorted together to reduce the potential gradient and, therefore, the EMG interference detected by the contacts 124. One of the remaining contacts 124 (e.g., the second or fourth contact 124b or 124d) can serve as a reference or ground electrode. In other embodiments, another electrode 430 attached to the patient (e.g., the dispersive electrode 130 of FIG. 2) can serve as the reference electrode.

Referring to FIG. 4B, the second amplifier assembly 440b is arranged with the contacts 124 in a TT circuit. The TT circuit includes three differential amplifiers (identified individually as first through third differential amplifiers 442a-c, respectively, and referred to collectively as differential amplifiers 442). The first and second contacts 124a and 124b can be electrically coupled to the first differential amplifier 442a, and the second and third contacts 124b and 124c can be electrically coupled to the second differential amplifier 442b. The first and second differential amplifiers 442a and 442b can in turn be coupled to a double-differential amplifier, i.e., the third differential amplifier 442c. In this TT amplifier assembly 440b, the contacts 124 are each connected to an input of a differential amplifier (which has a high impedance load), and therefore the TT amplifier assembly 440b is insensitive to electrode impedance. This reduces phase differences caused by electrode capacitance, and therefore causes the TT amplifier assembly 440b to be unaffected by electrode mismatches (e.g., when the electrodes are not positioned symmetrically).

In various embodiments, the gain of first stage amplifiers defined by first and second differential amplifiers 442a and 442b can be manipulated to compensate for non-uniform readings from the two electrode pairs, such as the first and second contacts 124a and 124b and the second and third contacts 124b and 124c. For example, the first stage amplifiers 442a and 442b can be varied to compensate for non-uniform tissue contact between the electrode pairs 124a-b and 124b-c. A second stage differential amplifier defined by the third differential amplifier 442c can then be used to at least substantially cancel out EMG signals (e.g., by matching the equal in amplitude but opposite in phase EMG potential gradient at each half of the circuit). At the same time, the TT amplifier assembly 440b is expected to produce higher ENG signals (e.g., higher than the QT amplifier assembly 440a of FIG. 4A), and improve the ENG to EMG ratio by tuning of the gains (e.g., using low noise first stage differential amplifiers). In other embodiments, two different pairs of contacts 124 can be electrically coupled to the first stage differential amplifiers, and/or additional contacts can be coupled in pairs to differential amplifiers that are in turn electrically coupled to a subset of differential amplifiers. As with the QT circuit of FIG. 4A, the fourth contact 124d and/or another electrode can serve as a reference/ground electrode.

In FIG. 4C, the third amplifier assembly 440c is arranged with the contacts 124 in an AT circuit. Similar to the TT circuit, the AT circuit includes two pairs of contacts 124 (e.g., the first and second contacts 124a and 124b and the second and third contacts 124b and 124c) electrically coupled to two corresponding differential amplifiers 442 (i.e., the first and second differential amplifiers 442a and 442b), which are in turn coupled to the third differential amplifier 442c. In addition, the output of the first stage differential amplifiers (i.e., the first and second differential amplifiers 442a and 442b) are also electrically coupled to controller 444. The controller 444 can allow the AT circuit to automatically compensate for electrode errors using a closed-loop control approach (i.e., automatic feedback gain adjustment). For example, the controller 444 can include two additional variable gain amplifiers, two rectifiers, a comparator, an integrator, and a feedback amplifier to provide the desired automatic feedback gain adjustment. The AT amplifier assembly 440c applies a frequency independent method, and therefore is expected to reduce EMG interference and at the same time retain neural information at the ENG bandwidth of interest. As discussed above with regard to the QT and TT circuit configurations, the fourth contact 124d and/or another electrode can serve as a reference electrode, and/or the contacts 124 can be arranged in different pairs than those shown in FIG. 4C.

Any one of the amplifier assemblies 440 can be incorporated into a digitizer (e.g., the digitizer 128 of FIGS. 1-3D) to differentiate ENG signals from EMG signals and other background noise, and thereby detect neural activity. The detected ENG signals can be transmitted to an extracorporeal device and displayed on a screen, monitor, or other type of display in real-time for an operator (e.g., a physician) to view during and/or after a procedure. In other embodiments, ENG signals can be filtered from the EMG signals using analog or digital filtering applied to the output signal, and the filtered ENG signals can be used in conjunction with amplifier neutralization. In further embodiments, high-order filtering may be used to separate ENG signals from slower EMG signals because the frequency spectra of the two signals overlap, but the peaks of their power spectral densities differs by about an order of magnitude. In still further embodiments, algorithms and/or artificial neural networks can be used to separate ENG signals from EMG signals.

Figure 5:
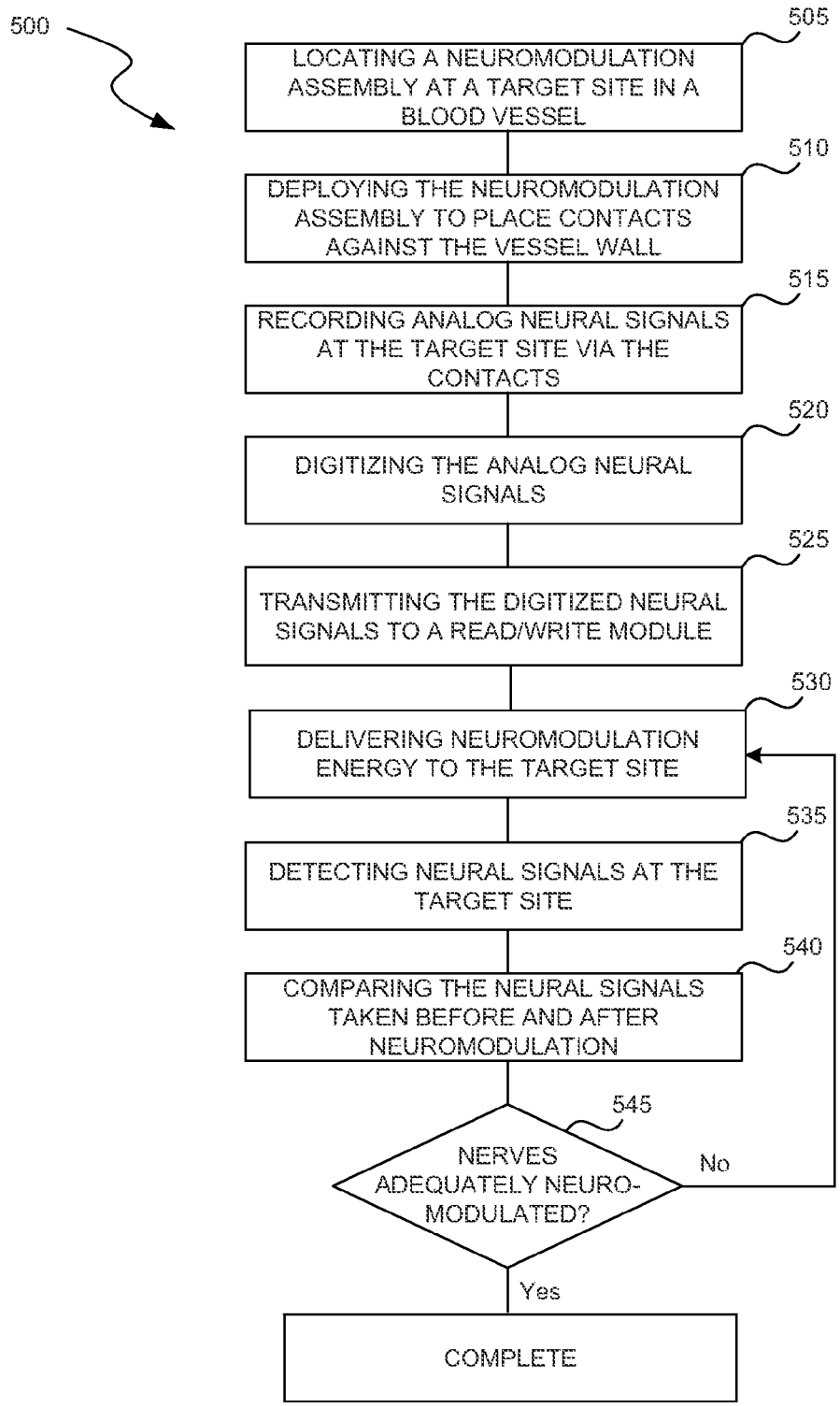
FIG. 5 is a block diagram illustrating a method of monitoring nerve activity in accordance with an embodiment of the present technology.

FIG. 5 is a block diagram illustrating a method 500 of monitoring nerve activity using the system 100 of one of the embodiments of FIGS. 1-4C or another suitable system in accordance with an embodiment of the present technology. The method 500 can include intravascularly placing a neuromodulation assembly (e.g., the neuromodulation assembly 120 of FIG. 1) at a target site in a blood vessel (block 505), and deploying the neuromodulation assembly from a delivery state (e.g., a low-profile configuration) to a deployed state (e.g., an expanded configuration) to place two or more contacts (e.g., electrodes) and/or other energy delivery elements at least substantially in contact with the vessel wall (e.g., as shown in FIG. 3D; block 510).

The method 500 can further include recording analog neural signals at the target site via the contacts (block 515), and digitizing the analog neural signals with a digitizer (e.g., the digitizer 128 of FIGS. 3A-3D) positioned proximate to the contacts (block 520). In certain embodiments, the contacts can be spaced along the neuromodulation assembly and communicatively coupled to the digitizer, and in other embodiments the contacts can be integrated with the digitizer such that the contacts and the digitizer define a single module. The digitizer can be attached to the neuromodulation catheter at a location such that the amplitude of the recorded analog neural signals remains above a level at which the analog neural signals can be accurately digitized from other signals detected by the contacts. The recorded electrical activity may include EMG signals from the surrounding muscle fibers and/or other background noise. Accordingly, an amplifier assembly can be used to filter the analog neural signal before the digitizing step. For example, the digitizer can include an amplifier assembly that is electrically coupled to the contacts in a QT, TT, and/or AT arrangement (e.g., as described above with reference to FIGS. 4A-4C).

The digitized neural signals can then be transmitted to an extracorporeal read/write module (e.g., the read/write module 130 of FIG. 1) where they can be viewed and/or analyzed by a clinician or a computer (block 525). In certain embodiments, the digitizer can include a telemetry module that wirelessly transmits the digitized neural signals to the read/write module. For example, the digitizer and the read/write module can be inductively coupled to each other. In other embodiments, the digitized neural signals can be transmitted to read/write module via wires that extend from the digitizer to the read/write module.

In various embodiments, neural activity can be detected from several locations at and/or proximate to the target site, and the digitized neural signals from each location can be transmitted to the read/write module. These digitized signals can be transmitted individually, or the digitizer may include a memory that stores a plurality of digitized neural signals and sends them together to the read/write module. At the read/write module and/or other device communicatively coupled thereto, the neural signals from the various locations can be averaged to provide a baseline ENG of neural activity before neuromodulation. In other embodiments, neural recordings can be taken from different pairs of contacts and compared to provide an understanding of the neural activity along the vessel and/or to select which contact pair or pairs provide the best ENG signals (e.g., the clearest or strongest ENG signals). If the recorded ENG signals are low or indeterminable, the operator may optionally stimulate neural activity with a short current pulse supplied by one of the contacts (e.g., a first electrode), and the other contacts (e.g., a second, third, and/or fourth electrode) can be used to record the resultant neural activity.

After a pre-neuromodulation ENG signal has been detected, the method 500 can continue by delivering neuromodulation energy to the target site (block 530). In certain embodiments, the same contacts that are used to detect the neural activity can be used to deliver the neuromodulation energy to the treatment site. In other embodiments, the neuromodulation assembly can include separate energy delivery elements dedicated to neuromodulation treatment, such as separate electrodes, cryotherapeutic applicators, ultrasound transducers, and/or radiation emitters.

The method 500 can further include detecting neural signals proximate to the treatment site after the neuromodulation energy has been applied (block 535). As discussed above, the neural signals can be detected by recording electrical activity via the contacts, filtering the recorded analog signals to distinguish the neural signals from other electrical activity, and digitizing the analog neural signals. The operator can optionally record neural activity from a plurality of different contact pairs and/or at a plurality of locations proximate to the target site, and the various neural recordings can be compared with each other and/or averaged.

The digitizer can transmit the digitized neural signals to the extracorporeal read/write module, and the post-neuromodulation ENG signals can then be compared with the ENG signals taken before neuromodulation (block 540). Decreases (e.g., substantial decreases) in the amplitude and/or other parameter of the ENG signals after neuromodulation may indicate sufficient treatment of nerves proximate to the target site. For example, a decrease in amplitude of the ENG signals of 20%, 30%, 40%, 50%, 60%, 70%, 80%, and/or over 90% may indicate sufficient treatment of the target nerves. Using this information, the method 500 can then determine whether the nerves have been adequately modulated (block 545). For example, if the amplitude observed in ENG is below a threshold value, then the neuromodulation step may have effectively modulated or stopped conduction of the adjacent nerves and the neuromodulation process can be considered complete. However, if nerve activity is detected above a threshold value, the process of neuromodulating (block 530) and monitoring the resultant nerve activity (block 535) can be repeated until the nerves have been effectively modulated. The method 500 can optionally be repeated after a time period (e.g., 5-30 minutes, 2 hours, 1 day, etc.) to confirm that the nerves were adequately ablated (e.g., rather than merely being stunned).

The method 500 and the system 100 (FIG. 1) used to implement the method 500 can monitor neural activity and deliver therapeutic energy to modulate nerves to provide real-time feedback of the effectiveness of a neuromodulation treatment. By digitizing the neural signals proximate to the place at which they are recorded (e.g., at the contacts), the method 500 can reduce attenuation and/or other distortion that the analog neural signals may incur had they been transmitted elsewhere before further filtering or processing. The method 500 also provides the recording and energy delivery steps in a single device (e.g., the neuromodulation catheter 102 (FIG. 1)). Accordingly, the method 500 can facilitate more efficient procedure times than if these steps were performed by two separate devices that would need to be delivered independently of each other to the treatment site. In various embodiments, the same elements (e.g., electrodes) can be used to provide both the recording and energy delivery function. In addition, the method 500 can differentiate ENG signals from EMG signals using recordings taken intravascularly positioned contacts.

Figure 6:
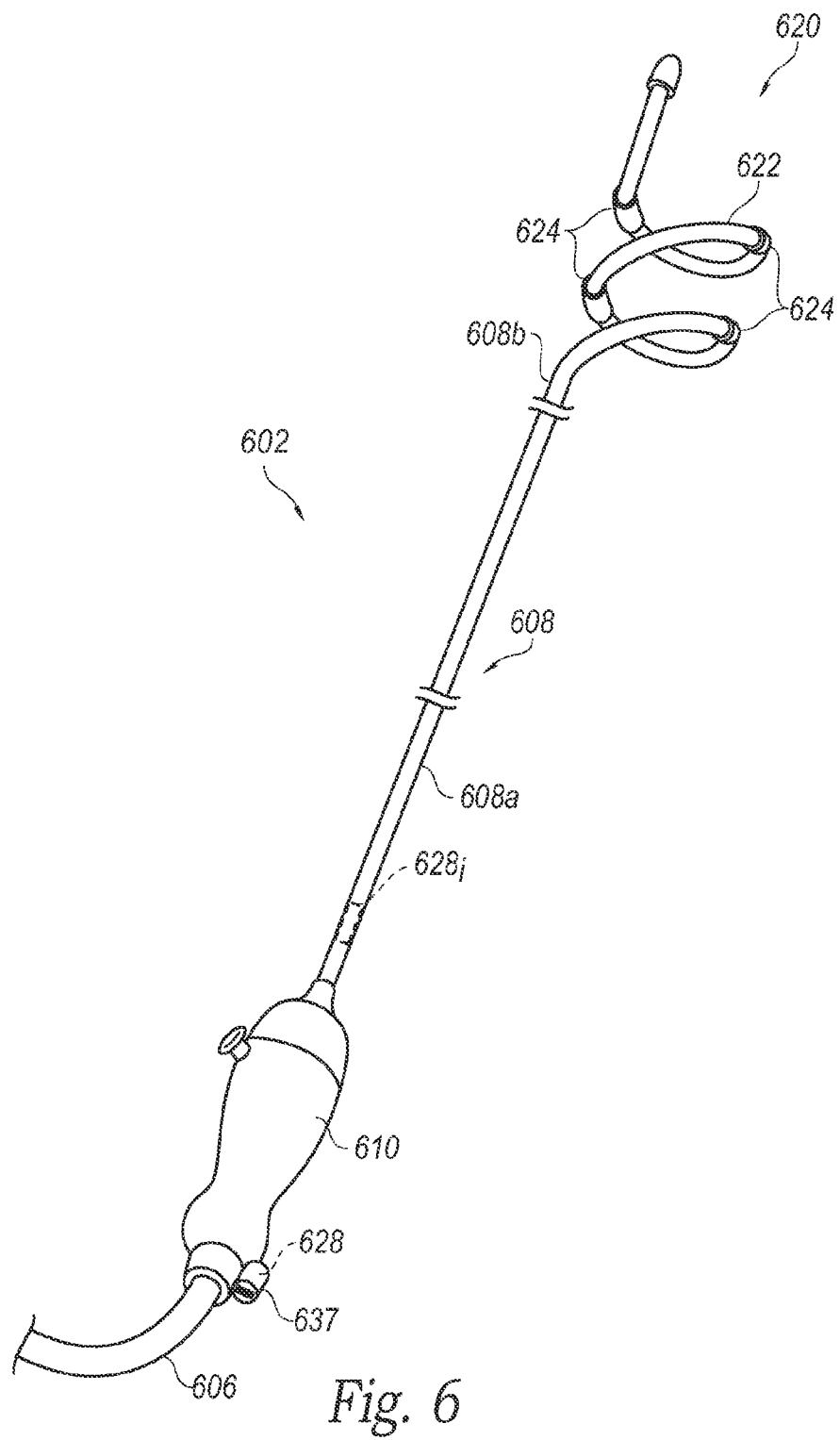
FIG. 6 is an isometric view of a neuromodulation catheter configured in accordance with another embodiment of the present technology.

FIG. 6 is an isometric view of a neuromodulation catheter 602 configured in accordance with another embodiment of the present technology. The neuromodulation catheter 602 can include various features generally similar to those of the neuromodulation catheter 102 described above with reference to FIGS. 1-4C. For example, the neuromodulation catheter 602 can include an elongated shaft 608 with a handle 610 at a proximal portion 608a of the shaft 608 and a neuromodulation assembly 620 at a distal portion 608b of the shaft 608. The neuromodulation assembly 620 can include a plurality of contacts 624 carried by a support member 622 that places the contacts 624 against an interior wall of a body lumen when the neuromodulation assembly 620 is in a deployed state. In certain embodiments, the contacts 624 can be electrodes that record analog neural signals and/or deliver therapeutic neuromodulation energy to nerves proximate to the target site.

The neuromodulation catheter 602 can further include a digitizer 628 that receives the analog signals from the contacts 624, filters the analog neural signals to provide ENG signals, and digitizes the analog neural signals into digital neural signals. In the embodiment illustrated in FIG. 6, the digitizer 628 is coupled to the handle 610 at the proximal portion 608a of the shaft 608. The digitizer 628 can therefore receive the analog neural signals from the contacts 624 via wires that extend along the length of the shaft 608. In other embodiments, the contacts 624 can be wirelessly coupled to the digitizer 628 via a telemetry module (not shown) operably coupled to the contacts 624. Once the neural signals have been received and digitized at the digitizer 628, the digitizer 628 can transmit the digitized neural signals to a separate read/write module (not shown, e.g., the read/write module 130 of FIG. 1) where they can be further processed and/or viewed by an operator. The digitized neural signals can be transmitted via signal wires that extend through a cable 606 attached to the handle 610 and/or a separate cable or wire that extends directly from the digitizer 628. In other embodiments, the digitizer 628 can include a telemetry module (not shown) that can wirelessly transmit the digitized neural signals to the read/write module.

As shown in FIG. 6, the digitizer 628 can be stored within a housing 637 that is separate from and releasably coupled to the handle 610. For example, the housing 637 may include an electrical connector (e.g., a phone connector) that is received by a corresponding port in the handle 610. This electrical connection allows the digitizer 628 to receive the analog signals recorded by the contacts 624 via wires that extend through the shaft 608. In other embodiments, the housing 637 can be attached to the exterior of the handle 610 using a temporary adhesive and/or a mechanical connector, without being hardwired to the contacts 624 connected to features of the handle 610. In this embodiment, the analog neural signals can be wirelessly transferred to the digitizer 628. Regardless of the manner in which the digitizer 628 is coupled to the contacts 624, the detachable housing 637 can be removed from the handle 610 after use so that the digitizer 628 can be used with other neuromodulation catheters. In other embodiments, the digitizer 628 may be integrated into the handle 610 itself. Though spaced further from the contacts 624 than the digitizers 128, 128$_i$ and 128$_{ii}$ of FIGS. 3A-3D, the digitizer 628 of FIG. 6 can still capture analog neural signals closer to the contacts 624 than a read/write module or computer spaced apart from the neuromodulation catheter 620, and thereby reduce errors that may otherwise be introduced into the neural recordings.

In other embodiments, the neuromodulation catheter 602 can include a digitizer positioned elsewhere on device. For example, FIG. 6 illustrates a digitizer 628$_i$ (shown in broken lines) positioned on the proximal portion 608a of the shaft 608. The digitizer 628$_i$ can be attached to an exterior surface of the shaft 608 similar to the digitizer shown in FIG. 3B, or can be positioned within the shaft 608. Similar to the digitizer 628 carried by the handle 610, the proximally positioned digitizer 628$_i$ can either be hardwired to the contacts 624 via wires that extend through the shaft 608, or may be wirelessly coupled to the contacts 624. The digitizer 628$_i$ can capture and digitize the analog signal relatively close to the contacts 624, and thereby at least partially reduce distortion in the ENG signal. In further embodiments, the 628$_i$ can be positioned along another portion of the shaft 608.

Figure 7:
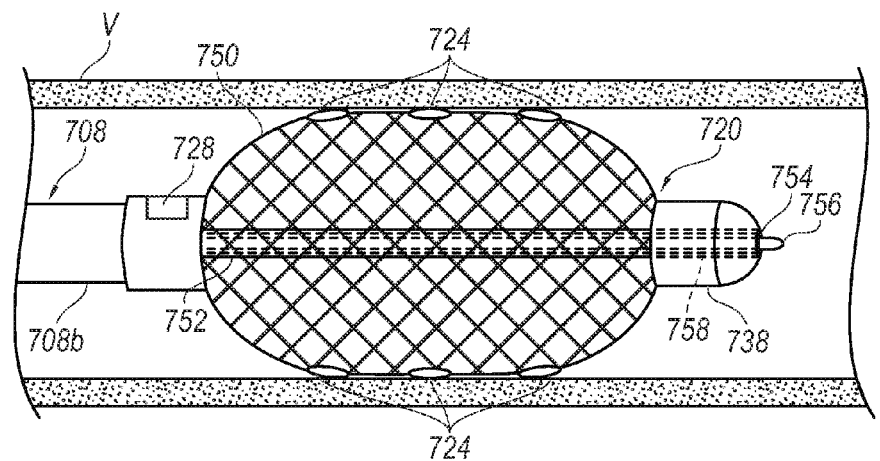
FIG. 7 is a side view of a distal portion of a neuromodulation catheter configured in accordance with yet another embodiment of the present technology.

FIG. 7 is a side view of a neuromodulation assembly 720 at a distal portion of a neuromodulation catheter configured in accordance with another embodiment of the present technology. The neuromodulation assembly 720 includes various features generally similar to those of the neuromodulation assembly 120 described above with reference to FIGS. 1-3D. For example, the neuromodulation assembly 720 can be attached to a distal portion 708b of a shaft 708, and can include a plurality of contacts 724 (e.g., electrodes) configured to contact a vessel wall V when the neuromodulation assembly 720 is in a deployed state (e.g., shown in FIG. 7). In addition, the neuromodulation assembly 720 can include a digitizer 728 carried by the distal portion 708b of the shaft 708 proximal to the contacts 724. In other embodiments, the digitizer 728 can be positioned elsewhere on the neuromodulation assembly 720.

In the embodiment illustrated in FIG. 7, the contacts 724 are supported by an expandable mesh structure 750. For example, the contacts 724 may be proximate to, adjacent to, adhered to, and/or woven into the mesh structure 750. In other embodiments, the contacts 724 may also be formed by the mesh structure 750 itself (e.g., the fibers of the mesh may be capable of delivering energy). Whether the contacts 724 are mounted on or integrated into the mesh structure 750, the mesh structure 750 can be expanded such that the contacts 724 contact with the vessel wall V. Once in contact with the vessel wall V, the contacts 724 may deliver power independently of each other (i.e., may be used in a monopolar fashion), either simultaneously or progressively, and/or may deliver power between any desired combination of the elements (i.e., may be used in a bipolar fashion). In addition, the contacts 724 can perform a nerve monitoring function by detecting neural activity before and/or after in energy delivery. In other embodiments, some of the contacts 724 on the mesh structure 750 can be configured solely for nerve recording and the other contacts can be configured for energy delivery.

At least some of the contacts 724 on the mesh structure 750 can be communicatively coupled to the digitizer 728 via signal wires or a wireless coupling means such that the digitizer 728 can receive the analog signals recorded by the contacts 724, filter and digitize the analog signals, and transmit the digitized neural signals to an extracorporeal device via a wired or wireless connection. In other embodiments, the digitizer 728 can be carried by the mesh structure 750, and can itself include contacts that record analog neural signals when placed in contact with the vessel wall V.

As shown FIG. 7, the neuromodulation assembly 720 can further include a tube 752 or other type of shaft that extends through the length of the mesh structure 750, and a distal member 738 (e.g., a collar, shaft, or cap) at the distal end portion of the mesh structure 750 coupled to the tube 752. The distal member 738 can include a rounded distal portion to provide atraumatic insertion of the neuromodulation assembly 720 into a vessel and an opening 754 that allows the neuromodulation assembly 720 to be threaded over a guide wire 756 for intravascular delivery to a target site. In addition, the shaft 708, the tube 752, the mesh structure 750, and/or the distal member 738 may have a lumen sized and shaped to slideably accommodate a control wire 758. The control wire 758 can facilitate the expansion and/or contraction of the mesh structure 750 when it is pulled or pushed (e.g., at the proximal end of the neuromodulation catheter). For example, pulling (i.e., an increase in tension) of control wire 758 may shorten the mesh structure 750 to increase its diameter placing it in an expanded configuration (e.g., FIG. 7), whereas pushing (i.e., an increase in compression) of control wire 758 may lengthen the mesh structure 750 to a compressed configuration. As shown in FIG. 7, the control wire 758 can be a hollow tube that can be passed over the guide wire 756. In other embodiments, the control wire 758 may be a solid structure (e.g., made from a metal or polymer). Further details and characteristics of neuromodulation assemblies with mesh structures are including in International Patent Application No. PCT/US2011/057153 (International Patent Application Publication No. WO2012/054862), which is herein incorporated by reference in its entirety.

Figure 8:
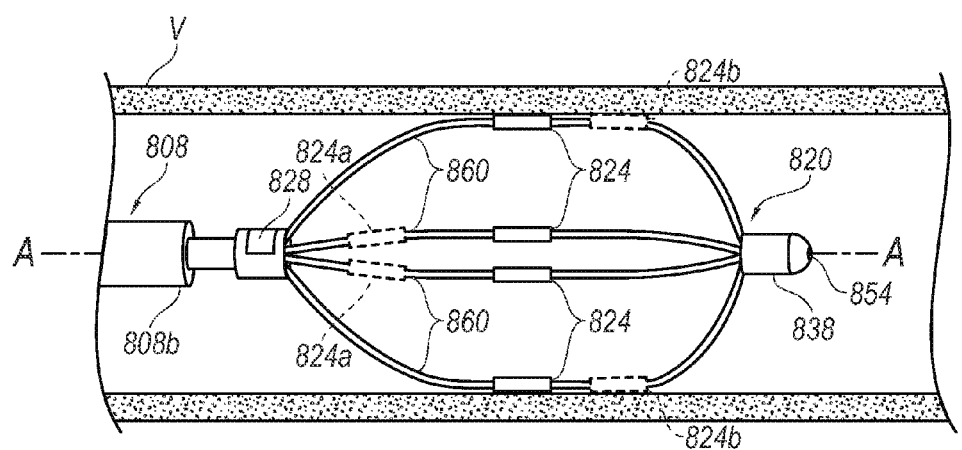
FIG. 8 is a side view of a distal portion of a neuromodulation catheter configured in accordance with a further embodiment of the present technology.

FIG. 8 is a side view of a neuromodulation assembly 820 at a distal portion of a neuromodulation catheter configured in accordance with yet another embodiment of the present technology. The neuromodulation assembly 820 includes various features generally similar to those of the neuromodulation assemblies 120 and 720 described above. For example, the neuromodulation assembly 820 can be attached to a distal portion 808b of a shaft 808, and can include a plurality of contacts 824 configured to be placed into contact with a vessel wall V when the neuromodulation assembly 820 is deployed within a vessel (e.g., FIG. 8). An atraumatic (e.g., rounded) distal member 838 can be attached to the distal portion of the neuromodulation assembly 820 and can include a distal guide wire opening 854 to facilitate intravascular delivery of the neuromodulation assembly 820 to a target site. In addition, the neuromodulation assembly 820 can include a digitizer 828 carried by the distal portion 808b of the shaft 808 and communicatively coupled to the contacts 824. In other embodiments, the digitizer 828 can be positioned elsewhere on the neuromodulation assembly 820.

In the embodiment illustrated in FIG. 8, the neuromodulation assembly 820 further includes a plurality of supports 860 that define an expandable basket structure and carry the contacts 824. The proximal ends of the supports 860 can be attached or otherwise connected to the distal portion 808b of the shaft 808, and the distal ends of the supports 860 can be attached or otherwise connected to the distal member 838. At least one of the distal portion 808b of the shaft 808 and the distal member 838 can be moveable along the longitudinal dimension A-A of the shaft 808 to transform the neuromodulation assembly 820 from a low-profile delivery state to an expanded deployed state in which the contacts 824 contact in the inner wall V of at a target site.

As shown in FIG. 8, the contacts 824 can be spaced angularly apart from each other around the longitudinal dimension A-A of the shaft 808 at a common area along the length of the longitudinal dimension A-A. This arrangement places the contacts 824 in contact with the vessel wall V to provide an at least substantially circumferential exposure (e.g., for neural recording and/or neuromodulation) in a common plane perpendicular to the longitudinal dimension A-A of the shaft 808. In other embodiments, the contacts 824 can have other suitable configurations. For example, one or more contacts 824 can be spaced along the length of the supports 860 to provide nerve monitoring and/or neuromodulation at different zones along the length of the vessel and/or the neuromodulation assembly 820 can include a different number of supports 860 than the four supports 860 illustrated in FIG. 8 (e.g., to provide nerves with more fully circumferential exposure the contacts 824). In further embodiments, the contacts 824 can be positioned in a staggered relationship relative to each other along the length of the neuromodulation assembly 820. For example, first electrodes 824a (shown in broken lines) at a proximal portion of two of the supports 860 can be longitudinally offset from second contacts 824b (shown in broken lines) on distal portions of two other longitudinal supports 860. The first electrodes 824a can also be angularly offset from the second electrodes 824b by, for example, 90° or some other suitable angle.

At least some of the contacts 824 on supports 860 can be communicatively coupled to the digitizer 828 via signal wires or a wireless coupling means such that the digitizer 828 can receive the analog signals recorded by the contacts 824, filter and digitize the analog signals, and transmit the digitized neural signals to an extracorporeal device via a wired or wireless connection. In other embodiments, the digitizer 828 can be carried by one of the supports 860, and can itself include contacts that record analog neural signals when placed in contact with the vessel wall V. In further embodiments, the neuromodulation assembly 820 can include a plurality of digitizers 828 with contacts integrated therein, and the digitizers 828 can be spaced along various portions of the supports 860 to detect neural signals along various portions of the vessel wall V.

The contacts 824 can be electrodes configured to provide both energy delivery (e.g., RF energy) and recording of electrical activity at the target site. In other embodiments, some of the contacts 824 can serve solely as contacts for detecting neural signals while others are configured for energy delivery. In further embodiments, at least some of the contacts 824 can be configured to provide a form of energy other than electrical current (e.g., RF energy) to the target site, while others can provide the nerve monitoring function. For example, at least some of the contacts 824 can be defined by radiation emitters that expose target nerves to radiation at a wavelength that causes a previously administered photosensitizer to react, such that it damages or disrupts the nerves. The radiation emitters can be optical elements coupled to fiber optic cables (e.g., extending through the shaft 808) for delivering radiation from a radiation source (e.g., an energy generator) at an extracorporeal location to the target tissue at the vessel, or may be internal radiation sources (e.g., LEDs) that are electrically coupled to a power source at an extracorporeal location via electrical leads within the shaft 808.

In embodiments where one or more of the contacts 824 are defined by radiation emitters, a photosensitizer (e.g., oxytetracycline, a suitable tetracycline analog, and/or other suitable photosensitive compounds that preferentially bind to neural tissue) can be administered to a patient (e.g., orally, via injection, through an intravascular device, etc.), and preferentially accumulate at selected nerves (e.g., rather than other tissues proximate to the selected nerves). For example, more of the photosensitizer can accumulate in perivascular nerves around a blood vessel than in the non-neural tissues of the blood vessel. The mechanisms for preferentially accumulating the photosensitizer at the nerves can include faster uptake by the nerves, longer residual times at the nerves, or a combination of both. After a desired dosage of the photosensitizer has accumulated at the nerves, the photosensitizer can be irradiated using contacts 824. The contacts 824 can deliver radiation to the target nerves at a wavelength that causes the photosensitizer to react such that it damages or disrupts the nerves. For example, the photosensitizer can become toxic upon exposure to the radiation. Because the photosensitizer preferentially accumulates at the nerves and not the other tissue proximate the nerves, the toxicity and corresponding damage is localized primarily at the nerves. This form of irradiative neuromodulation can also or alternatively be incorporated in any one of the neuromodulation assemblies described herein. Further details and characteristics of neuromodulation assemblies with radiation emitters are included in U.S. patent application Ser. No. 13/826,604, which is incorporated herein by reference in its entirety.

Figure 9:
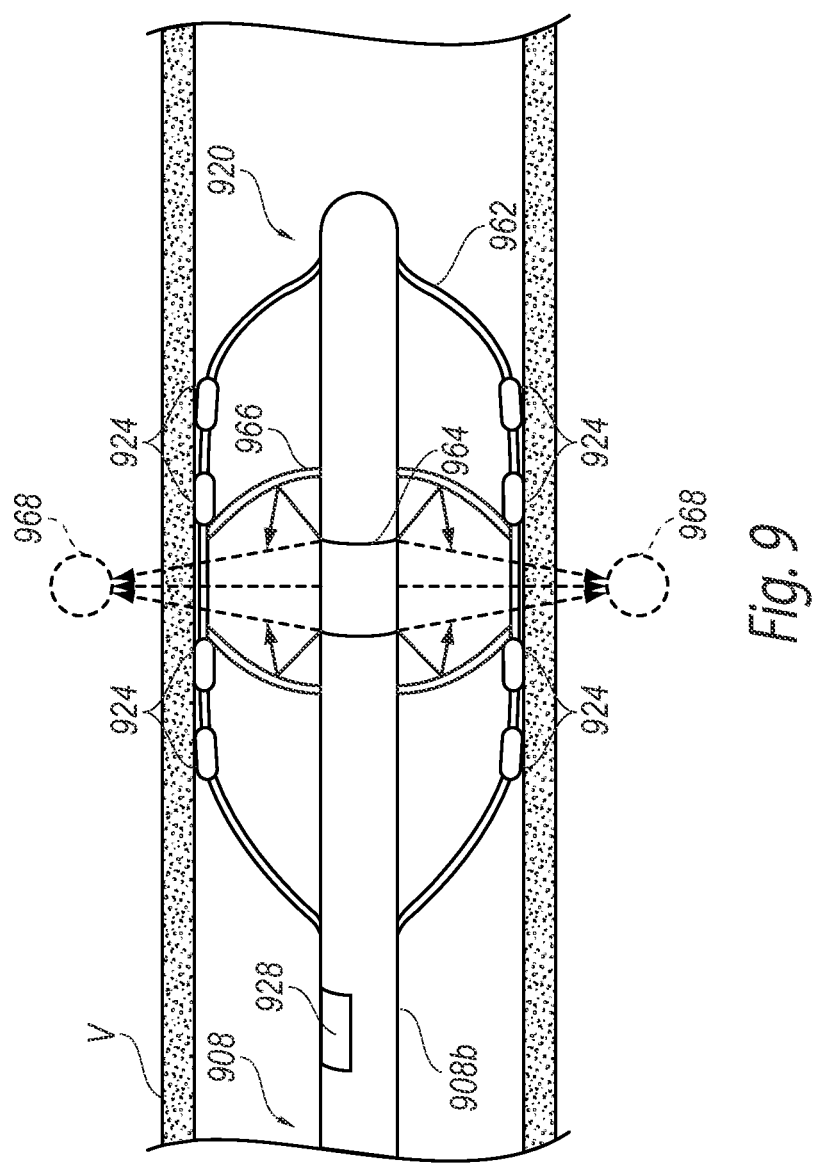
FIG. 9 is a side view of a distal portion of a neuromodulation catheter configured in accordance with yet another embodiment of the present technology.

FIG. 9 is a side view of a neuromodulation assembly 920 at a distal portion of a neuromodulation catheter configured in accordance with a further embodiment of the present technology. The neuromodulation assembly 920 includes various features generally similar to the features of the neuromodulation assemblies 120, 720 and 820 described above. For example, the neuromodulation assembly 920 can be attached to a distal portion 908*b* of a shaft 908, and can include a plurality of contacts 924 configured to be placed into contact with a vessel wall V when the neuromodulation assembly 920 is deployed within a vessel (e.g., FIG. 9). In the embodiment illustrated in FIG. 9, the contacts 924 are carried by an outer expandable body 962 (e.g., a balloon) that positions the contacts 924 against a vessel wall V when the expandable body 962 is deployed (e.g., inflated or otherwise expanded) within the vessel. In addition, the neuromodulation assembly 920 can include a digitizer 928 carried by the distal portion 908*b* of the shaft 908 and communicatively coupled to the contacts 924. At least some of the contacts 924 carried by the expandable body 962 can be communicatively coupled to the digitizer 828 via signal wires or a wireless coupling means such that the digitizer 928 can receive the analog signals recorded by the contacts 924, filter and digitize the analog signals, and transmit the digitized neural signals to an extracorporeal device via a wired or wireless connection. In other embodiments, one or more digitizers 928 can be carried by the expandable body 962, and can include contacts that record analog neural signals when placed in contact with the vessel wall V. In other embodiments, one or more digitizers 928 can be positioned elsewhere on the neuromodulation assembly 920.

As shown in FIG. 9, the shaft 908 and/or another suitable elongated member connected to the shaft 908 can extend at least partially through the expandable body 962 and carry an ultrasound transducer 964. The ultrasound transducer 964 may be configured to provide therapeutically effective energy (e.g., HIFU) and, optionally, provide imaging information that may facilitate placement of the transducer 964 relative to a blood vessel, optimize energy delivery, and/or provide tissue feedback (e.g. to determine when treatment is complete). Further, depending on the particular arrangement of the ultrasound transducer 964, the lesion created by the application of ultrasound energy may be limited to very specific areas (e.g., focal zones or focal points) on the periphery of the vessel wall V or on the nerves themselves. For example, it is expected that the average ultrasound intensity for neural modulation (e.g., ablation of renal nerves) may be in the range of about 1-4 $kW/cm^2$ and may be delivered for a total of 10-60 seconds to create one focal lesion.

In the embodiment illustrated in FIG. 9, the neuromodulation assembly 920 further includes an inner expandable body 966 (e.g., a balloon) positioned within the outer expandable body 962 and around the ultrasound transducer 964. The inner expandable body 966 can be filled with a sound-conducting medium (e.g. water, a conductive medium, etc.) and act as an acoustic lens and transmission media for the emitted ultrasonic energy. As indicated by the arrows, the waves emitted by the ultrasound transducer 964 can be formed into one or more focal beams focusing on corresponding focal points or regions 968 (e.g., about 0-5 mm deep in the surrounding tissue). In other embodiments, other features (e.g., an acoustically reflective material) can be used to form the waves into one or more focal beams.

As shown in FIG. 9, the outer expandable body 962 may be configured to position the contacts 924 away from the waves emitted by the ultrasound transducer 964 to avoid undesirably heating the contacts 924. Optionally, the outer expandable body 962 can be filled with a gas to contain the energy emitted by the ultrasound transducer 964 and inhibit it from escaping in the undesired directions. This form of ultrasound-based neuromodulation can also or alternatively be incorporated in any one of the neuromodulation assemblies described above or below. Additional features and alternative embodiments of ultrasound-induced neuromodulation devices are disclosed in U.S. patent application Ser. No. 12/940,0922 (U.S. Patent Publication No. 2011/0112400), which is incorporated herein by reference in its entirety.

Figure 10:
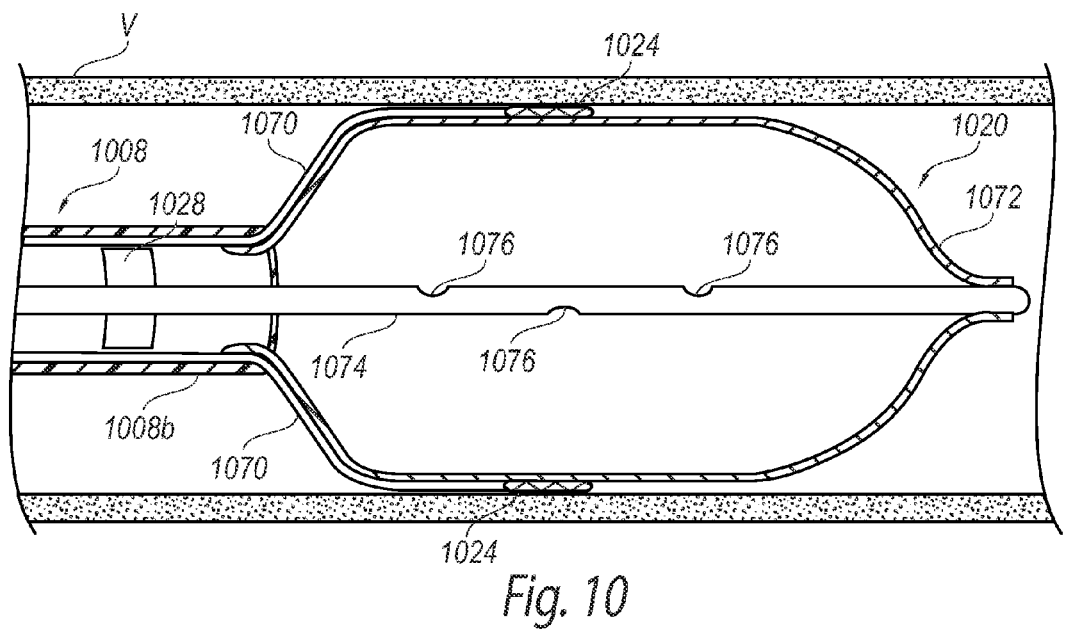
FIG. 10 is a partial cross-sectional side view of a distal portion of a neuromodulation catheter configured in accordance with a further embodiment of the present technology.

FIG. 10 is a partial cross-sectional side view of a neuromodulation assembly 1020 at a distal portion of a neuromodulation catheter configured in accordance with yet another embodiment of the present technology. The neuromodulation assembly 1020 includes various features generally similar to the features of the neuromodulation assemblies 120, 720, 820 and 920 described above. For example, the neuromodulation assembly 1020 can be attached to a distal portion 1008b of a shaft 1008, and can include a plurality of contacts 1024 configured to be placed into contact with a vessel wall V when the neuromodulation assembly 1020 is deployed within a vessel (e.g., FIG. 10). As shown in FIG. 10, the contacts 1024 can be electrically coupled to corresponding conductive leads 1070 (e.g., electrical wires) that extend through or along the shaft 1008. The leads 1070 can operably couple the contacts 1024 to an energy source (e.g., the energy generator 126 of FIG. 1) and/or a digitizer 1028 at the distal portion 1008b of the shaft 1008. The digitizer 1028 can receive the analog signals recorded by the contacts 1024, filter and digitize the analog signals, and transmit the digitized neural signals to an extracorporeal device via a wired or wireless connection.

As shown in FIG. 10, the neuromodulation assembly 1020 can further include a cryogenic applicator 1072 (e.g., a balloon or other expandable member) that can expand radially outward to press or otherwise contact the inner surface of the vessel wall V. For example, the cryogenic applicator 1072 can define at least a portion of an expansion chamber in which a refrigerant expands or otherwise flows to provide cryogenic cooling. A supply lumen 1074 can be fluidly coupled to a refrigerant source (e.g., a refrigerant cartridge or canister; not shown) at its proximal end portion, and may be sized to retain at least a portion of the refrigerant that reaches the expansion chamber at a high pressure liquid state. The supply lumen 1074 can include one or more orifices or openings 1076 from which refrigerant can expand into the expansion chamber, or refrigerant can be configured to expand from a distal opening of a capillary tube (not shown) extending from the supply lumen 1074. In various embodiments, the openings 1076 may have a cross-sectional area less than that of the supply lumen 1074 to impede the flow of refrigerant proximate the expansion chamber, thereby increasing the pressure drop of the refrigerant entering the expansion chamber and concentrating the refrigeration power at the cryogenic applicator 1072. For example, the openings 1076 can be sized relative to the area and/or length of an exhaust lumen (e.g., defined by a distal portion of the shaft 1008) to provide a sufficient flow rate of refrigerant, produce a sufficient pressure drop when the refrigerant enters the expansion chamber, and allow for sufficient venting of expanded refrigerant through the shaft 1008 to establish and maintain cooling at the cryogenic applicator 1072.

In operation, a liquid refrigerant can expand into a gaseous phase as it passes through the openings 1076 of the supply lumen 1074 into the expansion chamber (defined by at least a portion of the cryogenic applicator 1072), thereby inflating the cryogenic applicator 1072. The expansion of the refrigerant causes a temperature drop in the expansion chamber, thereby forming one or more cooling zones around at least a portion of the cryogenic applicator 1072. In various embodiments, the cooling zones created by the cryogenic applicator 1072 can provide therapeutically effective cooling to nerves proximate to the vessel wall V, while the contacts 1024 serve a nerve monitoring function. In other embodiments, the contacts 1024 can be replaced a plurality of digitizers 1028 can be carried by the exterior surface of the cryogenic applicator 1072, and can include contacts that record analog neural signals when placed in contact with the vessel wall V. In further embodiments, the cryogenic applicator 1072 can be a non-expandable member, such a cryoprobe at the distal portion 1008b of the shaft 1008 (e.g., a FREEZOR catheter available from Medtronic, Inc. of Minneapolis, Minn.).

In additional embodiments, the contacts 1024 can be configured to provide resistive heating in and/or at the tissue to raise the temperatures at hyperthermic zones in the vessel wall V and the surrounding neural fibers to provide therapeutically-effective neuromodulation, and the cryogenic applicator 1072 can be configured to form non-therapeutic cooling zones before, during, and/or after the delivery of hyperthermic energy by the contacts 1024. For example, concurrently with the application of hyperthermic energy via the contacts 1024, the cooling zone can be provided at a relatively low refrigeration power, e.g., a power less than that required to induce neuromodulation. The cooling zone can cool the contacts 1024 and/or the body tissue at or proximate to the target site (e.g., the inner surface of vessel wall V). The cooling zone provided by the cryogenic applicator 1072 is expected to maintain lower temperatures, and thereby reduce thermal trauma in the tissue proximate the inner surface of the vessel wall V during hyperthermic neuromodulation. The hyperthermic zone may also extend or focus more on the exterior area of the vessel wall V where the nerves reside. Therefore, the neuromodulation assembly 1020 can provide a reverse thermal gradient across a portion of the vessel wall V to provide hyperthermic neuromodulation at a depth in the tissue, while reducing potential hyperthermal effects on the vessel tissue closer to the neuromodulation assembly 1020.

The cryotherapeutic neuromodulation and/or cryogenic cooling described above can also or alternatively be incorporated in any one of the neuromodulation assemblies described above. Further details and characteristics of neuromodulation assemblies with cryogenic applicators are included in International Patent Application No. PCT/US2011/057514 and U.S. patent application Ser. No. 13/458,859, each of which is incorporated herein by reference in its entirety.

Figure 11:
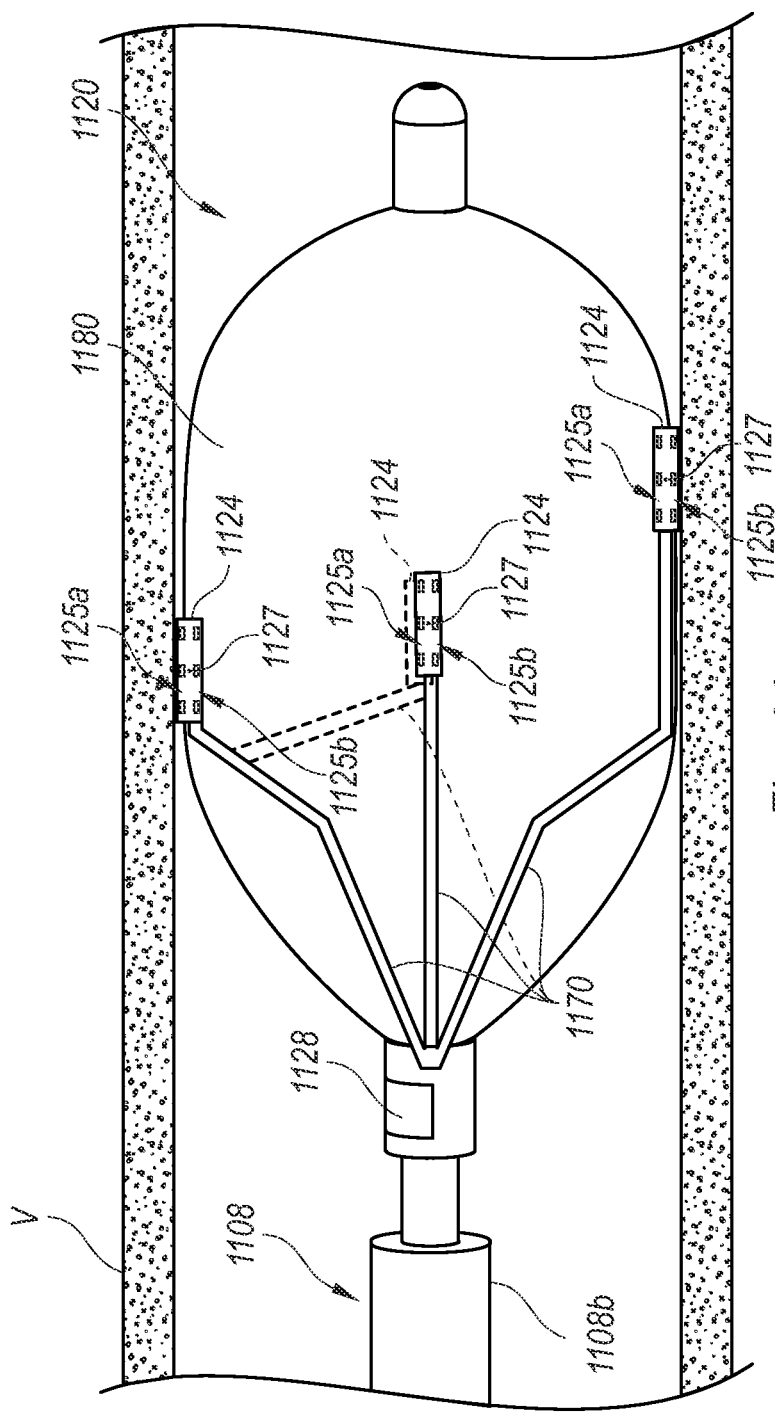
FIG. 11 is a side view of a distal portion of a neuromodulation catheter configured in accordance with yet another embodiment of the present technology.

FIG. 11 is a side view of a neuromodulation assembly 1120 at a distal portion of a neuromodulation catheter configured in accordance with yet another embodiment of the present technology. The neuromodulation assembly 1120 includes various features generally similar to the features of the neuromodulation assemblies 120, 720, 820, 920 and 1020 described above. For example, the neuromodulation assembly 1120 can be attached to a distal portion 1108b of a shaft 1108, and can include a plurality of contacts 1124 configured to be placed into contact proximate to a vessel wall V when the neuromodulation assembly 1120 is deployed within a vessel. As shown in FIG. 11, the neuromodulation assembly 1120 can further include a balloon 1180 or other expandable member that carries the contacts 1124. The balloon 1180 can be inflated with a fluid to place the contacts 1124 in contact with the vessel wall V and, optionally, occlude the vessel. For example, the balloon 1180 can be inflated by injecting a gas into the balloon 1180 via an inflation lumen (not shown) that extends along the length of the shaft 1108. In other embodiments, a fluid (e.g., a gas, a cryogenic fluid) can be circulated through the balloon 1180 to inflate the device.

As shown in FIG. 11, each contact 1124 can be a bipolar element having one or more oppositely biased contact pairs. For example, the contacts 1124 can each have a row of positive contacts 1125a and a row of negative contacts 1125b. In operation, a small electrical field is established between the positive contacts 1125*a* and the negative contacts 1125*b*. Each contact 1124 can also include a thermistor 1126. The contacts 1124 with the various contacts 1125*a-b* and thermistors 1126 can be flex circuits attached to a balloon 1180 or printed directly onto the balloon 1080.

The neuromodulation assembly 1120 can include a digitizer 1128 carried by the distal portion 1108*b* of the shaft 1108 and communicatively coupled to the contacts 1124. At least some of the contacts 1124 carried by the balloon 1180 can be communicatively coupled to the digitizer 128 such that the digitizer 1128 can receive the analog signals recorded by the contacts 1124, filter and digitize the analog signals, and transmit the digitized neural signals to an extracorporeal device via a wired or wireless connection. In other embodiments, one or more digitizers 1128 can be carried by the balloon 1180, and can include contacts that record analog neural signals when placed in contact with the vessel wall V. In other embodiments, one or more digitizers 1128 can be positioned elsewhere on the neuromodulation assembly 1120.

As further shown in FIG. 11, the plurality of contacts 1124 can be electrically coupled to a corresponding plurality of leads 1170 that are coupled to or positioned about the expandable member 1180. In various embodiments, the leads 1170 can be part of a flex circuit that easily expands or collapses with the expandable member 1180. The leads 1170 can be electrically coupled to an energy source (e.g., the energy generator 126 of FIG. 1) and/or the digitizer 1128 at the distal portion 1108*b* of the shaft 1108. Accordingly, the contacts 1124 can provide both a nerve recording function and a neuromodulation function.

In the embodiment illustrated in FIG. 11, the contacts 1124 are defined by individual bipolar point electrodes that are spaced at multiple lengthwise and angular positions relative to the outer surface of the balloon 1180 and the vessel wall V. For example, the four contacts 1124 shown in FIG. 11 can be angularly offset from each other by about 90°. In other embodiments, the contacts 1124 can be angularly offset from each other by different degrees (e.g., 60°, 80°, 180°, etc.) depending on the number of contacts 1124 and/or their relative spacing along the length of the balloon 1180. The lengthwise and/or angularly offset contacts 1124 can provide non-continuous circumferential neuromodulation and/or neural recording without having to reposition the neuromodulation assembly 1120. The illustrated embodiment shows four contacts 1124, but other embodiments can include different numbers of contacts (e.g., 1-12 contacts 1124). In further embodiments, the contacts 1124 can have other suitable configurations on the outer surface of the balloon 1180, and/or the contacts 1124 may have other suitable structures. For example, in certain embodiments one or more of the contacts 1124 can be defined by circular electrodes and/or spiral-shaped electrodes that extend around the outer surface of the balloon 1180. Such configurations can provide partial or full circumferential neuromodulation and/or neural recording along the vessel wall V.

III. RENAL NEUROMODULATION

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable target sites during a treatment procedure. The target site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a target site in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed energy, microwave energy, optical energy, focused ultrasound energy (e.g., high-intensity focused ultrasound energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular or intraluminal), optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., micro-needles) that can be retracted or otherwise blocked prior to deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

III. RELATED ANATOMY AND PHYSIOLOGY

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 12:
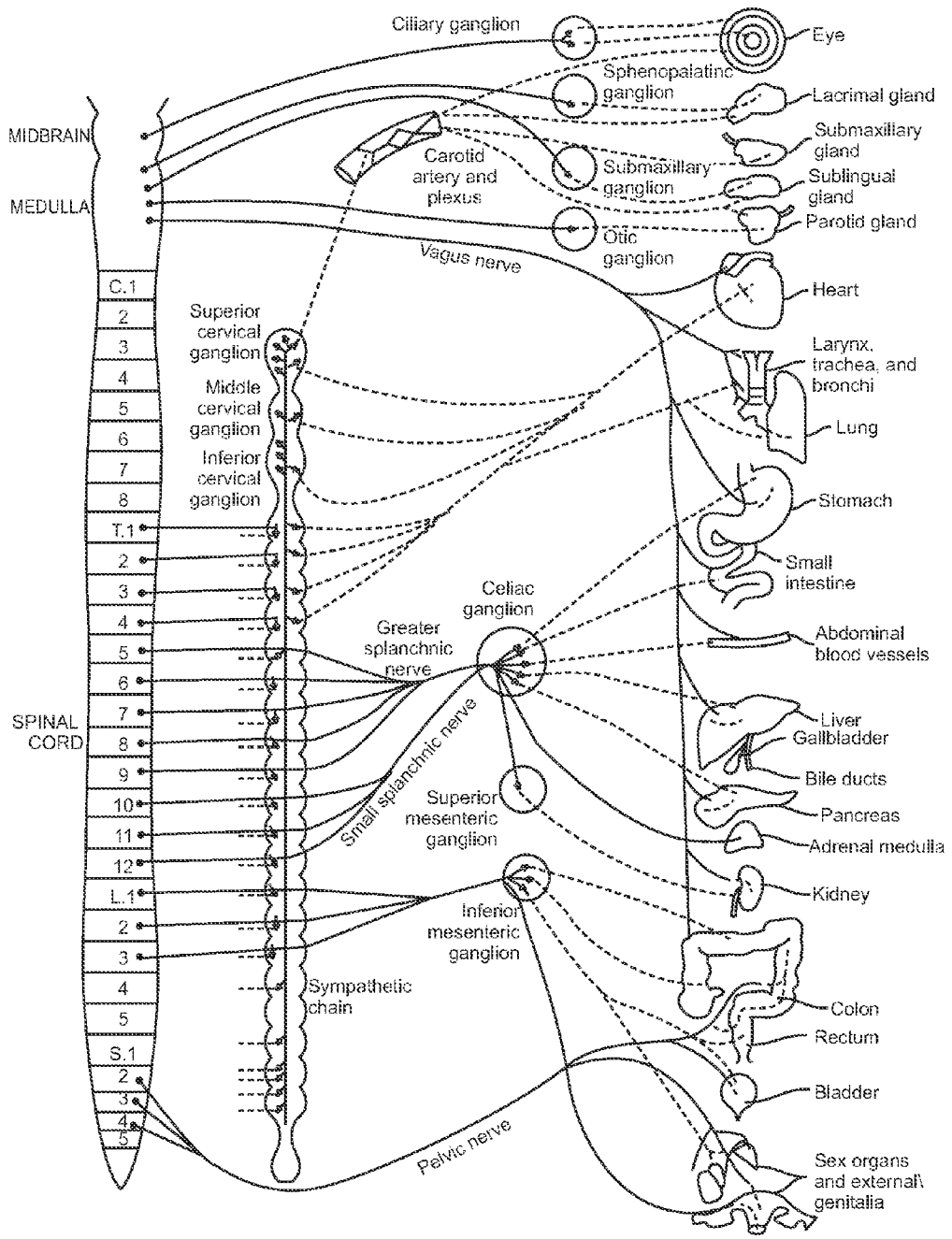
FIG. 12 is a conceptual illustration of the sympathetic nervous system (SNS) and how the brain communicates with the body via the SNS.

As shown in FIG. 12, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 13:
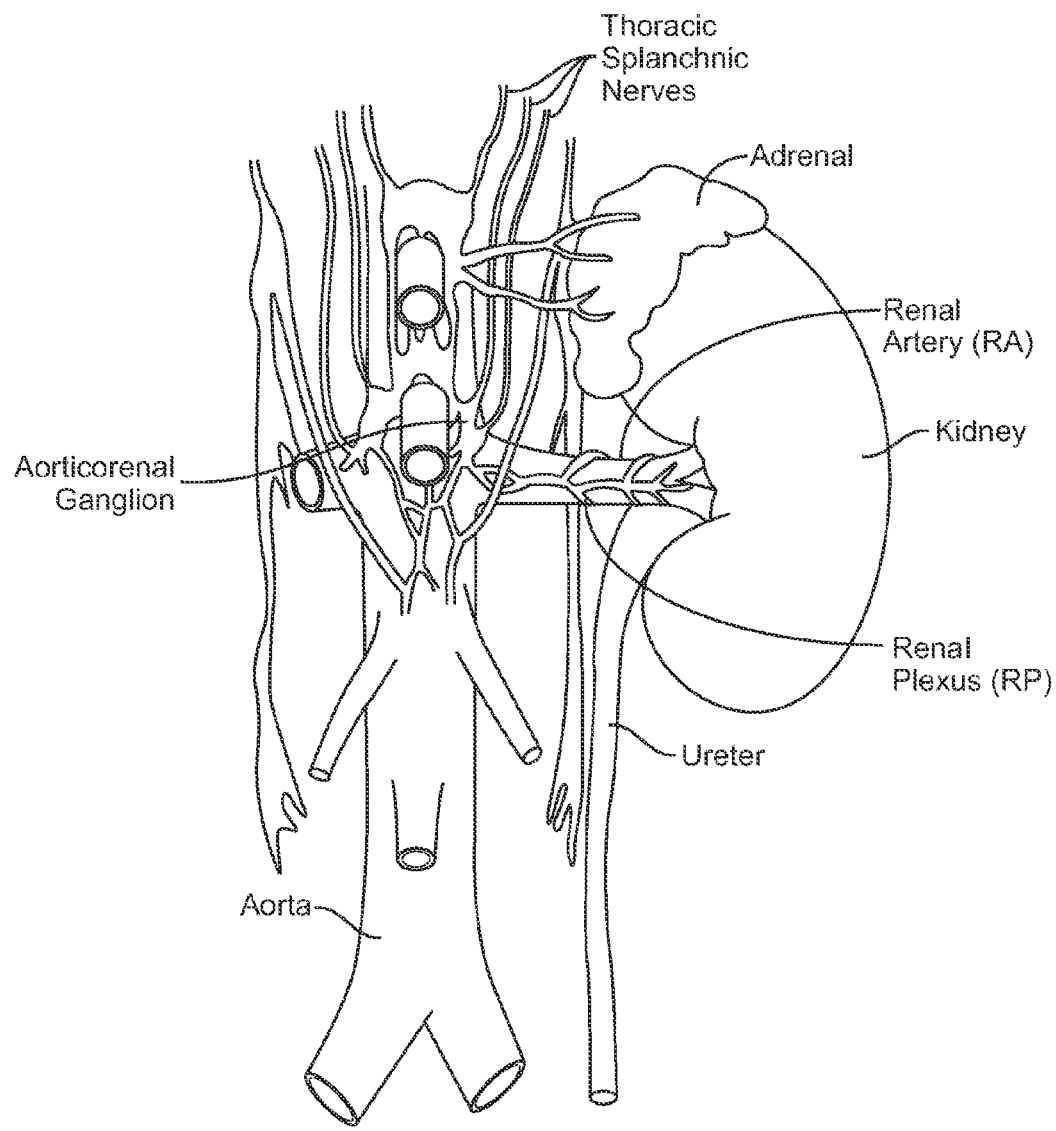
FIG. 13 is an enlarged anatomic view of nerves innervating a left kidney to form the renal plexus surrounding the left renal artery.

As FIG. 13 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease.

This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 14A:
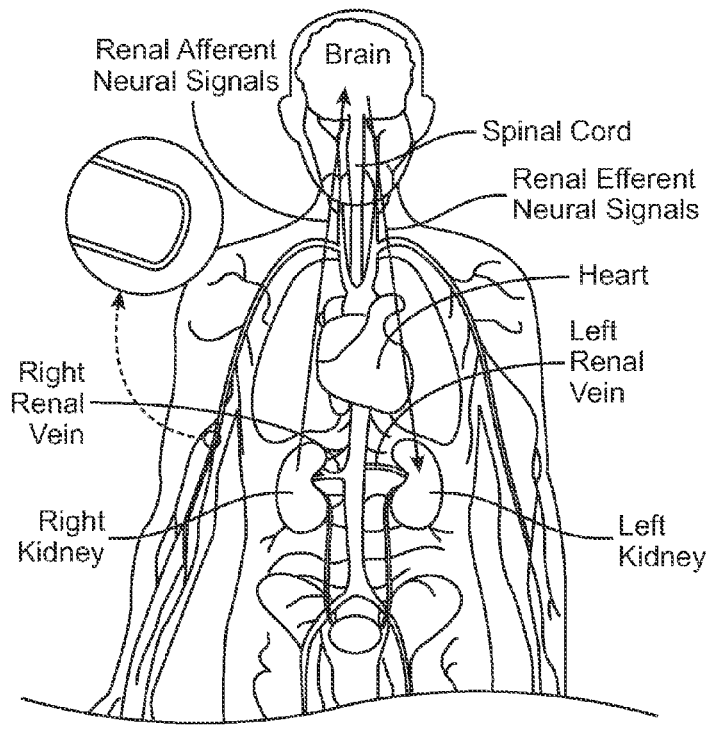
FIGS. 14A and 14B are anatomic and conceptual views, respectively, of a human body depicting neural efferent and afferent communication between the brain and kidneys.
Figure 14B:
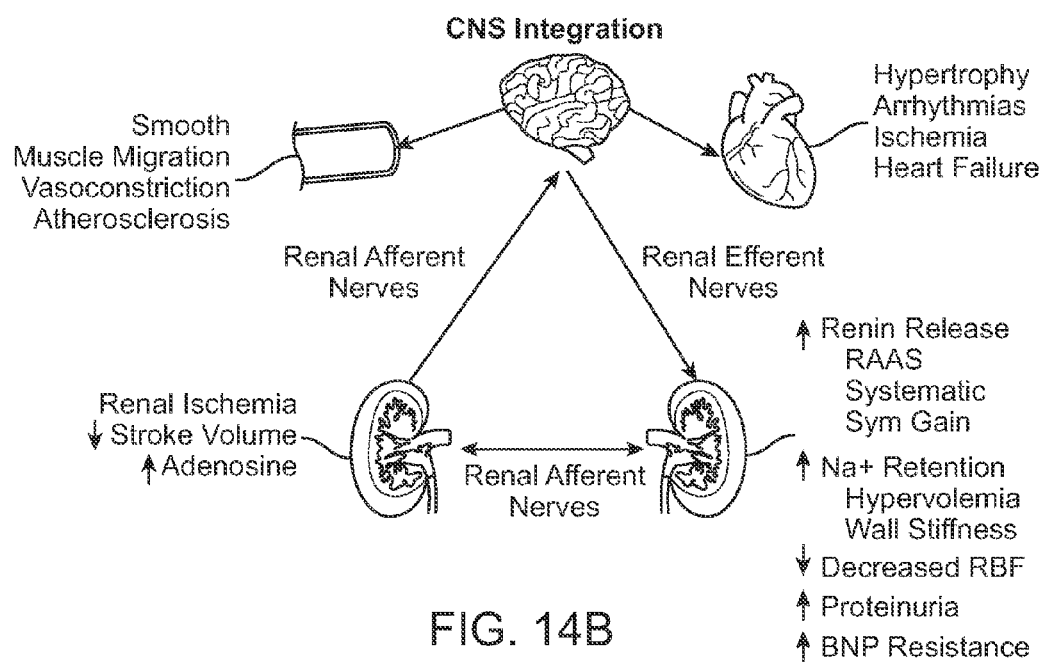

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 14A and 14B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 12. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 15A:
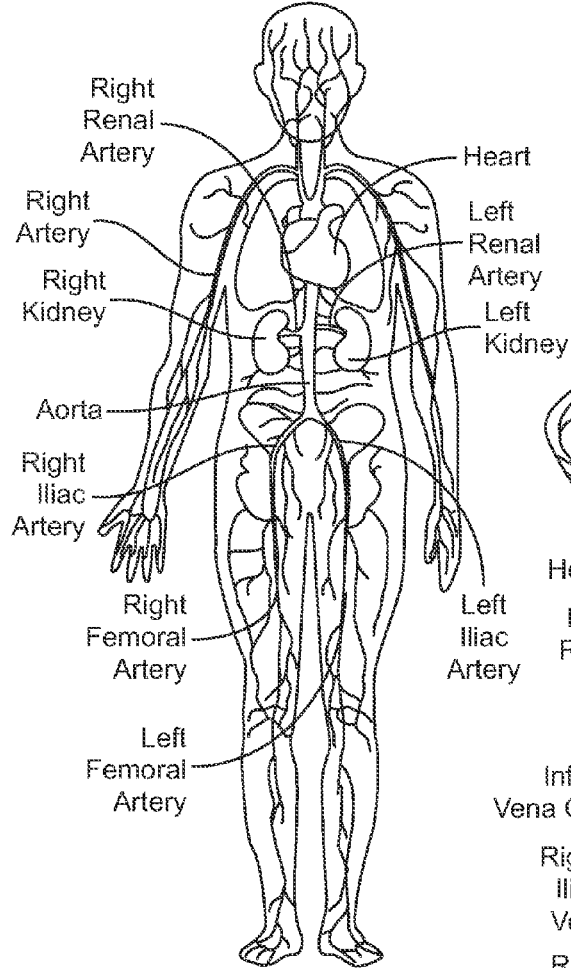
FIGS. 15A and 15B are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 15A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 15B:
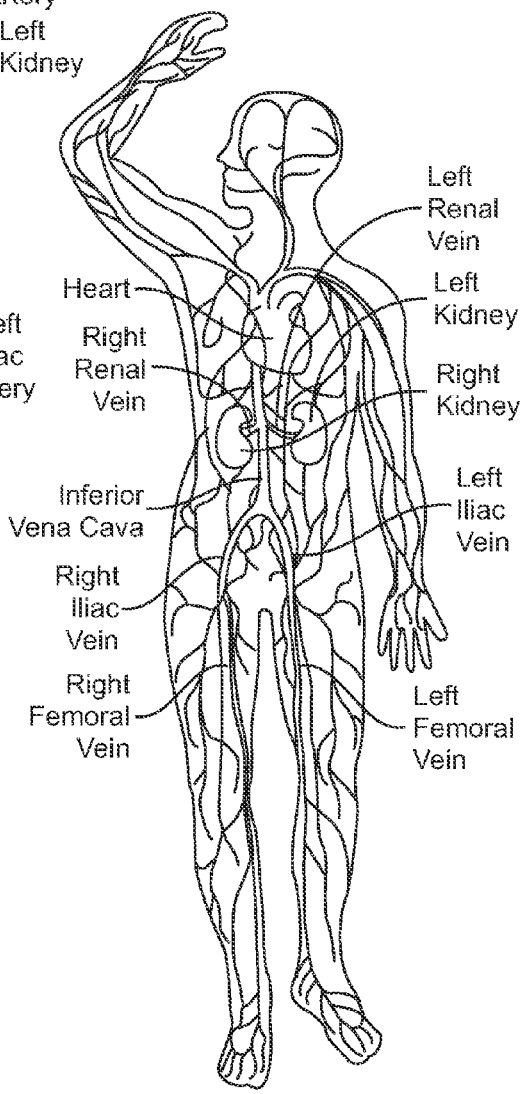

As FIG. 15B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

IV. ADDITIONAL EXAMPLES

1. A neuromodulation catheter, comprising:
   a handle;
   an elongated shaft attached to the handle, the shaft having a distal portion and a proximal portion, wherein at least the distal portion is configured to be moved within a lumen of a blood vessel of a human patient;
   an array of contacts at the distal portion of the shaft, wherein the contacts are configured to detect analog neural signals from nerves along the blood vessel while the contacts are within the blood vessel; and
   a digitizer at the handle or the shaft, wherein the digitizer is configured to receive the analog neural signals from the contacts, digitize the analog neural signals into digital neural signals, and transmit the digital neural signals to a read/write module external to the patient.

2. The neuromodulation catheter of example 1 wherein the digitizer is at the distal portion of the elongated shaft.

3. The neuromodulation catheter of example 1 wherein the digitizer is at the distal portion of the elongated shaft proximal to the contacts.

4. The neuromodulation catheter of example 1 wherein the digitizer is at the handle.

5. The neuromodulation catheter of example 4 wherein the digitizer is configured to be detachable from the handle for reuse with other neuromodulation catheters.

6. The neuromodulation catheter of example 1 wherein the digital neural signals comprise electroneurogram (ENG) signals, and wherein the digitizer is configured to filter signals received from the contacts to differentiate the ENG signals from electromyogram (EMG) signals before transmitting the digital neural signals to the read/write module.

7. The neuromodulation catheter of example 1 wherein the digitizer is configured to filer signals received from the contacts using an amplifier assembly having a quasi-tripole (QT), true-tripole (TT), and/or adaptive-tripole (AT) arrangement to detect electroneurogram (ENG) signals.

8. The neuromodulation catheter of example 1 wherein the digitizer comprises an analog to digital circuit.

9. The neuromodulation catheter of example 1 wherein the digitizer has a cross-sectional dimension of about 9-25 $mm^2$.

10. The neuromodulation catheter of example 1 wherein the digitizer further comprises a telemetry module configured to wirelessly transmit the digitized signals from within the patient to the read/write module.

11. The neuromodulation catheter of example 1 wherein the digitizer is inductively coupled to the read-write module.

12. The neuromodulation catheter of example 1 wherein the digitizer includes the contacts.

13. The neuromodulation catheter of example 12 wherein the digitizer is one of a plurality of digitizers, wherein each digitizer includes a plurality of contacts, and wherein the plurality of digitizers are at the distal portion of the shaft.

14. The neuromodulation catheter of example 1, further comprising at least one energy delivery element at the distal portion of the elongated shaft, wherein the energy delivery element is configured to deliver neuromodulation energy to a target site within the blood vessel of the patient.

15. The neuromodulation catheter of example 14 wherein the energy delivery element comprises a cryotherapeutic applicator, an ultrasound delivery element, and/or an RF electrode.

16. The neuromodulation catheter of example 1 wherein the contacts are further configured to deliver neuromodulation energy the nerves along the blood vessel of the patient and detect the analog neural signals before and/or after the delivery of the neuromodulation energy.

17. The neuromodulation catheter of example 1, further comprising a support member at the distal portion of the shaft, wherein the support member has a spiral shape and is configured to contact an interior wall of the blood vessel when the support member is in a deployed state, wherein the contacts are spaced apart from each other along a length of the support member, and wherein the contacts are configured to deliver neuromodulation energy to the nerves along the blood vessel.

18. The neuromodulation catheter of example 1, further comprising a plurality of supports that define a basket structure at the distal portion of the shaft, wherein the contacts are arranged along the supports and, and wherein the supports are configured to contact an interior wall of the blood vessel when the supports are in a deployed state.

19. The neuromodulation catheter of example 1, further comprising a mesh structure at the distal portion of the shaft, wherein the mesh structure is configured to contact an interior wall of the blood vessel when the mesh structure is in a deployed state, and wherein the contacts are arranged along the mesh structure.

20. The neuromodulation catheter of example 1, further comprising a balloon at the distal portion of the shaft, wherein the balloon carries the contacts and is configured to place the contacts into contact with an interior wall of the blood vessel when expanded.

21. The neuromodulation catheter of example 1 wherein:
   the digital neural signals comprise electroneurogram (ENG) signals, and wherein the digitizer is configured to filter signals received from the contacts to differentiate the ENG signals from electromyogram (EMG) signals before transmitting the digital neural signals to the read/write module; and the digitizer further comprises a telemetry module configured to wirelessly transmit the digitized signals from within the patient to the read/write module.

22. The neuromodulation catheter of example 1 wherein:

the digitizer is at the distal portion of the elongated shaft proximal to the contacts, wherein the digitizer chip comprises—
- a telemetry module configured to wirelessly transmit the digitized signals from within the patient to the read/write module;
- an analog to digital circuit; and
- a amplifier assembly configured to filter signals received from the contacts to differentiate the electroneurogram (ENG) signals from electromyogram (EMG) signals before transmitting the digital neural signals to the read/write module; and the contacts are further configured to deliver neuromodulation energy to the nerves along the blood vessel of the patient and detect the analog neural signals before and/or after the delivery of the neuromodulation energy.

23. A neuromodulation catheter, comprising:
- a shaft configured to be moved through a lumen of a blood vessel of a human and having a distal portion and a proximal portion;
- a plurality of contacts at the distal portion of the shaft, wherein the contacts are configured to detect analog neural measurements from within a blood vessel in a human; and
- a digitizer electrically coupled to the contacts and attached to the catheter at a location such that the amplitude of the analog neural signals remains above a level at which the analog neural signals can be accurately digitized from other signals detected by the contacts, wherein the digitizer is configured to digitize the analog neural measurements and produce digital neural signals.

24. The catheter of example 23 wherein the digitizer is attached to the shaft of the catheter.

25. The catheter of example 23, further comprising a handle attached to the shaft, wherein the digitizer is attached to the handle.

26. The catheter of example 23 wherein the digitizer comprises an analog to digital circuit configured to digitized the analog neural signals, a memory to store the digital neural signals, and a telemetry system configured to transmit the digital neural signals to an extracorporeal receiver located outside of the human.

27. A neuromodulation system, comprising:
- a neuromodulation catheter having a distal portion and a proximal portion and configured to be moved through a lumen of a blood vessel of a human, wherein the neuromodulation catheter comprises—
  - a plurality of contacts configured to detect analog neural measurements from within the blood vessel of the human; and
  - a digitizer operably coupled to the contacts, wherein the digitizer is configured to digitize the analog neural measurements and produce digital neural signals; and
- a read/write module communicatively coupled to the digitizer and configured to receive the digital signals of the neural measurements.

28. The neuromodulation system of example 27 wherein the digitizer and the read/write module are wirelessly coupled to each other.

29. The neuromodulation system of example 27 wherein contacts are integrated with the digitizer.

30. The neuromodulation system of example 27 wherein the distal portion of the neuromodulation catheter comprises at least one energy delivery element configured to deliver to therapeutically-effective neuromodulation energy to neural fibers at a target site within the blood vessel of the human.

31. The neuromodulation system of example 30 wherein the contacts define the at least one energy delivery element such that the contacts are configured to deliver neuromodulation energy to neural fibers and detect neural measurements before and after delivering the neuromodulation energy.

32. The neuromodulation system of example 27 wherein the digitizer is at the distal portion of the neuromodulation catheter proximate to the contacts.

33. The neuromodulation system of example 27 wherein the digitizer comprises a amplifier assembly configured to filter signals received from the contacts to differentiate the electroneurogram (ENG) signals from electromyogram (EMG) signals before transmitting digital neural signals to the read/write module.

34. A neuromodulation system, comprising:
- a neuromodulation catheter having—
  - an elongated shaft having a distal portion and a proximal portion, wherein at least the distal portion is configured to be moved within a lumen of a blood vessel of a human;
  - an array of contacts at the distal portion of the shaft, wherein the contacts are configured to detect analog neural signals from within the blood vessel; and
  - a transmitter operably coupled to the contacts; and
- a guide catheter configured to extend over the neuromodulation catheter and deliver at least the distal portion of the shaft to a target site within the blood vessel, wherein the guide catheter comprises—
  - a digitizer configured to receive the analog neural signals from the transmitter, digitize the analog neural signals into digital neural signals, and transmit the digital neural signals to a read/write module external to the human.

35. A method of detecting neural activity from within a blood vessel of a human, the method comprising:
- delivering a distal portion of a neuromodulation catheter to a target site within the blood vessel of the human, wherein the distal portion comprises a plurality of contacts;
- recording analog neural signals with the contacts;
- digitizing recorded analog neural signals via a digitizer operably coupled to the contacts, wherein the digitizer is integrated with the neuromodulation catheter; and
- transmitting the digital neural signals to a read/write module external to the human.

36. The method of example 35 wherein digitizing the recorded analog neural signals is performed within the human.

37. The method of example 35, further comprising filtering the recorded analog neural signals with the digitizer to differentiate electroneurogram (ENG) signals from electromyogram (EMG) signals.

38. The method of example 35, further comprising filtering the recorded analog neural signals with the digitizer using quasi-tripole (QT), true-tripole (TT), and/or adaptive-tripole (AT) signal processing techniques to detect electroneurogram (ENG) signals, wherein the analog neural signals are filtered before digitizing.

39. The method of example 35, further comprising:
  delivering neuromodulation energy to a target site within the blood vessel of the human via at least one energy delivery element, wherein the recording, digitizing, and transmitting steps are performed before and after delivery of the neuromodulation energy; and
  comparing electroneurogram (ENG) signals recorded before and after delivery of the neuromodulation energy.

40. The method of example 39, further comprising delivering neuromodulation energy at the target site for a second time when there is not a decrease in the ENG signal detected after energy delivery.

41. The method of example 39 wherein the target site is a first target site, and wherein the method further comprises:
  repositioning the energy delivery element to a second target site within the blood vessel; and
  delivering neuromodulation energy to the second target site via the energy delivery element, wherein the recording, digitizing, and transmitting steps are performed before and after delivery of the neuromodulation energy.

42. The method of example 35 wherein:
  recording analog neural signals further comprises recording a plurality of analog neural signals taken during a plurality of different time intervals;
  digitizing recorded analog neural signals further comprises digitizing each of the recorded neural signals;
  transmitting the digital neural signals to the read/write module further comprises transmitting each of the digital neural signals to the read/write module after each time interval; and
  averaging the digital neural signals at the read/write module to determine nerve activity proximate to the contacts.

43. The method of example 35, further comprising comparing electroneurogram (ENG) signals taken at different time intervals.

44. The method of example 35 wherein transmitting the digital neural signals comprises wirelessly transmitting the digital neural signals from within the human to the read/write module.

45. The method of example 35 wherein transmitting the digital neural signals comprises inductively transmitting the digital neural signals from within the human to the read/write module.

46. The method of example 35 wherein the neuromodulation catheter comprises a handle at the proximal portion of the neuromodulation catheter, and wherein the digitizer is at the handle.

47. The method of example 35, further comprising delivering neuromodulation energy via at least one energy delivery element to a target site within the blood vessel of the human, wherein the recording, digitizing, and transmitting steps are performed before and/or after delivery of the neuromodulation energy.

48. The method of example 47 wherein delivering the neuromodulation energy via the energy delivery element comprises delivering the neuromodulation energy via the plurality of contacts.

49. The method of example 47 wherein the energy delivery element comprises a radiation emitter, and wherein delivering neuromodulation energy via the energy delivery element comprises delivering radiation to a vessel wall at the target site.

50. The method of example 47 wherein the energy delivery element comprises an ultrasound transducer, and wherein delivering neuromodulation energy via the energy delivery element comprises delivering ultrasound waves to a vessel wall at the target site.

51. The method of example 47 wherein the energy delivery element comprises a cryotherapeutic applicator, and wherein delivering neuromodulation energy via the energy delivery element comprises delivering cryotherapeutic cooling to a vessel wall at the target site.

52. A neuromodulation catheter, comprising:
  a shaft configured to be moved through a lumen of a blood vessel of a human and having a distal portion from which therapeutic energy is delivered to a target site within the blood vessel; and
  a digitizer at the distal portion of the shaft and having a plurality of contacts, wherein the contacts are configured to detect analog neural measurements from within a blood vessel in a human, and wherein the digitizer is configured to digitize the analog neural measurements and produce digital neural signals.

53. The neuromodulation catheter of claim 52 wherein the contacts are configured to deliver the therapeutic energy to the target site.

54. The neuromodulation catheter of example 52 wherein the digitizer is one of a plurality of digitizers at the distal portion of the shaft.

55. The neuromodulation catheter of example 52 wherein the digitizer comprises an analog to digital circuit configured to digitize the analog neural signals, a memory to store the digital neural signals, and a telemetry system configured to transmit the digital neural signals to an extracorporeal receiver located outside of the human.

V. CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back,"

"vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

I claim:

1. A neuromodulation catheter, comprising: a handle; an elongated shaft attached to the handle, the shaft having a distal portion and a proximal portion, wherein at least the distal portion is configured to be moved within a lumen of a blood vessel of a human patient; an array of contacts at the distal portion of the shaft, wherein the contacts are configured to detect analog neural signals from nerves along the blood vessel while the contacts are within the blood vessel; and a digitizer at the handle of the shaft, wherein the digitizer is configured to receive the analog neural signals from the contacts, digitize the analog neural signals into digital neural signals comprising electroneurogram (ENG) signals, and transmit the digital neural signals to a read/write module external to the patient, wherein the digitizer is configured to filter signals received from the contacts to differentiate the ENG signals from electromyogram (EMG) signals before transmitting the digital neural signals to the read/write module.

2. The neuromodulation catheter of claim 1 wherein the digitizer is configured to be detachable from the handle for reuse with other neuromodulation catheters.

3. The neuromodulation catheter of claim 1 wherein the digitizer is configured to filter signals received from the contacts using an amplifier assembly having a quasi-tripole (QT), true-tripole (TT), or adaptive-tripole (AT) arrangement to detect electroneurogram (ENG) signals.

4. The neuromodulation catheter of claim 1 wherein the digitizer comprises an analog to digital circuit.

5. The neuromodulation catheter of claim 1 wherein the digitizer has a cross-sectional dimension of about 9-25 mm$^2$.

6. The neuromodulation catheter of claim 1 wherein the digitizer further comprises a telemetry module configured to wirelessly transmit the digitized signals from within the patient to the read/write module.

7. The neuromodulation catheter of claim 1 wherein the digitizer is inductively coupled to the read/write module.

8. The neuromodulation catheter of claim 1, further comprising at least one energy delivery element at the distal portion of the elongated shaft, wherein the energy delivery element is configured to deliver neuromodulation energy to a target site within the blood vessel of the patient.

9. The neuromodulation catheter of claim 8 wherein the energy delivery element comprises an RF electrode.

10. The neuromodulation catheter of claim 1 wherein the contacts are further configured to deliver neuromodulation energy to the nerves along the blood vessel of the patient and detect the analog neural signals before or after the delivery of the neuromodulation energy.

11. The neuromodulation catheter of claim 1, further comprising a support member at the distal portion of the shaft, wherein the support member has a spiral shape and is configured to contact an interior wall of the blood vessel when the support member is in a deployed state, wherein the contacts are spaced apart from each other along a length of the support member, and wherein the contacts are configured to deliver neuromodulation energy to the nerves along the blood vessel.

12. The neuromodulation catheter of claim 1, further comprising a plurality of supports that define a basket structure at the distal portion of the shaft, wherein the contacts are arranged along the supports and, and wherein the supports are configured to contact an interior wall of the blood vessel when the supports are in a deployed state.

13. The neuromodulation catheter of claim 1, further comprising a mesh structure at the distal portion of the shaft, wherein the mesh structure is configured to contact an interior wall of the blood vessel when the mesh structure is in a deployed state, and wherein the contacts are arranged along the mesh structure.

14. The neuromodulation catheter of claim 1, further comprising a balloon at the distal portion of the shaft, wherein the balloon carries the contacts and is configured to place the contacts into contact with an interior wall of the blood vessel when expanded.

15. The neuromodulation catheter of claim 1 wherein the digitizer comprises: a telemetry module configured to wirelessly transmit the digitized signals from within the patient to the read/write module; an analog to digital circuit; and an amplifier assembly configured to filter the signals received from the contacts to differentiate the electroneurogram (ENG) signals from the electromyogram (EMG) signals before transmitting the digital neural signals to the read/write module; and wherein the contacts are further configured to deliver neuromodulation energy to the nerves along the blood vessel of the patient and detect the analog neural signals before or after the delivery of the neuromodulation energy.

16. A neuromodulation system, comprising: a neuromodulation catheter having a proximal portion and a distal portion configured to be moved through a lumen of a blood vessel of a human, wherein the neuromodulation catheter comprises: a plurality of contacts at the distal portion of the catheter and configured to detect analog neural measurements from within the blood vessel of the human; and a digitizer at the proximal portion of the catheter and operably coupled to the contacts, wherein the digitizer is configured to digitize the analog neural measurements and produce digital neural signals; and a read/write module communicatively coupled to the digitizer and configured to receive the digital signals of the neural measurements, wherein the digitizer comprises an amplifier assembly configured to filter signals received from the contacts to differentiate electroneurogram (ENG) signals from electromyogram (EMG) signals before transmitting digital neural signals to the read/write module.

17. The neuromodulation system of claim 16 wherein the digitizer and the read/write module are wirelessly coupled to each other.

18. The neuromodulation system of claim 16 wherein the distal portion of the neuromodulation catheter comprises at least one energy delivery element configured to deliver to therapeutically-effective neuromodulation energy to neural fibers at a target site within the blood vessel of the human.

19. The neuromodulation system of claim 18 wherein the contacts define the at least one energy delivery element such that the contacts are configured to deliver neuromodulation energy to neural fibers and detect neural measurements before and after delivering the neuromodulation energy.

20. The neuromodulation system of claim 16 wherein:
the neuromodulation catheter further comprises a plurality of energy delivery elements configured to deliver therapeutically-effective neuromodulation energy to neural fibers at a target site within the blood vessel of the human.

21. A neuromodulation system, comprising: a neuromodulation catheter having: an elongated shaft having a distal portion and a proximal portion, wherein at least the distal portion is configured to be moved within a lumen of a blood vessel of a human; an array of contacts at the distal portion of the shaft, wherein the contacts are configured to detect analog neural signals from within the blood vessel; and a transmitter operably coupled to the contacts; and a guide catheter configured to extend over the neuromodulation catheter and deliver at least the distal portion of the shaft to a target site within the blood vessel, wherein the guide catheter comprises: a digitizer configured to receive the analog neural signals from the transmitter, digitize the analog neural signals into digital neural signals comprising electroneurogram (ENG) signals, and transmit the digital neural signals to a read/write module external to the human, wherein the digitizer is configured to filter signals received from the transmitter to differentiate the ENG signals from electromyogram (EMG) signals before transmitting the digital neural signals to the read/write module.

* * * * *